(12) United States Patent
Wachter et al.

(10) Patent No.: US 7,346,387 B1
(45) Date of Patent: Mar. 18, 2008

(54) METHODS FOR IMPROVED SELECTIVITY IN PHOTO-ACTIVATION AND DETECTION OF MOLECULAR DIAGNOSTIC AGENTS

(75) Inventors: Eric A. Wachter, Oak Ridge, TN (US); Walter G. Fisher, Knoxville, TN (US); H. Craig Dees, Knoxville, TN (US)

(73) Assignee: Provectus Devicetech, Inc., Knoxville, TN (US)

( * ) Notice: Subject to any disclaimer, the term of this patent is extended or adjusted under 35 U.S.C. 154(b) by 0 days.

(21) Appl. No.: 09/072,963

(22) Filed: May 5, 1998

Related U.S. Application Data

(62) Division of application No. 08/741,370, filed on Oct. 30, 1996, now Pat. No. 5,832,931.

(51) Int. Cl.
  *A61B 6/00*    (2006.01)
(52) U.S. Cl. ...................................... 600/476
(58) Field of Classification Search ................ 600/473, 600/310, 407, 476; 356/317, 300, 318; 250/458.1, 250/459.1; 372/4, 9
See application file for complete search history.

(56) References Cited

U.S. PATENT DOCUMENTS 4,822,335 A    4/1989  Kawai et al.

(Continued)

FOREIGN PATENT DOCUMENTS

| WO | WO 96/38410 | 12/1996 |
|---|---|---|
| WO | WO 97/09043 | 3/1997 |
| WO | US97/19249 | 10/1997 |

OTHER PUBLICATIONS

International Search Report re EP Application No. 97 94 8121, mailed Nov. 5, 1999.
Abstract: Bodaness, R.S. et al, "The Two-Photon Induced Fluorescence of the Tumor Localizing Photosensitizer Hematoporphyrin Derivative via 1064 nm Photons from a 20 ns Q-Switched Nd-YAG Laser," *Biochemical and Biophysical Research Communications*, vol. 126, No. 1, pp. 346-351, Jan. 16, 1985.

(Continued)

*Primary Examiner*—Eric F. Winakur
*Assistant Examiner*—Michael Rozanski
(74) *Attorney, Agent, or Firm*—Cook, Alex, McFarron, Manzo, Cummings & Mehler, Ltd.

(57) ABSTRACT

A method for the imaging of a particular volume of plant or animal tissue, wherein the plant or animal tissue contains at least one photo-active molecular agent. The method comprises the steps of treating the particular volume of the plant or animal tissue with light sufficient to promote a simultaneous two-photon excitation of the photo-active molecular agent contained in the particular volume of the plant or animal tissue, photo-activating at least one of the at least one photo-active molecular agent in the particular volume of the plant or animal tissue, thereby producing at least one photo-activated molecular agent, wherein the at least one photo-activated molecular agent emits energy, detecting the energy emitted by the at least one photo-activated molecular agent, and producing a detected energy signal which is characteristic of the particular volume of plant or animal tissue. The present invention also provides a method for the imaging of a particular volume of material, wherein the material contains at least one photo-active molecular agent.

19 Claims, 13 Drawing Sheets

U.S. PATENT DOCUMENTS

| | | | | |
|---|---|---|---|---|
| 4,973,848 | A | | 11/1990 | Kolobanov et al. |
| 5,034,613 | A | * | 7/1991 | Denk et al. ............... 250/458.1 |
| 5,124,944 | A | * | 6/1992 | Suzuki et al. ............... 365/113 |
| 5,192,980 | A | * | 3/1993 | Dixon et al. ................ 356/326 |
| 5,231,984 | A | | 8/1993 | Santana-Blank |
| 5,483,338 | A | | 1/1996 | Wachter et al. |
| 5,522,868 | A | * | 6/1996 | Buckley et al. ............... 607/94 |
| 5,558,666 | A | | 9/1996 | Dewey et al. |
| 5,586,981 | A | | 12/1996 | Hu |
| 5,912,257 | A | * | 6/1999 | Prasad et al. ............... 514/356 |
| 5,991,021 | A | * | 11/1999 | Mukherjee et al. ......... 356/317 |

OTHER PUBLICATIONS

Abstract: Lenz, P., "In Vivo Excitation of Photosensitizers by Infrared Light," *Photochemistry and Photobiology*, vol. 62, No. 2, pp. 333-338, Aug. 1995.

Abstract: Fisher, W.G. et al, "Simultaneous Two-Photon Activation of Type-I Photodynamic Therapy Agents," *Photochemistry and Photobiology*, vol. 66, No. 2, pp. 141-155, Aug. 1997.

Abstract: Bhawalkar, J.D. et al, "Two-Photon Photodynamic Therapy," *Journal of Clinical Laser Medicine and Surgery*, vol. 15, No. 5, pp. 201-204, 1997.

E.A. Wachter, Fisher et al. "Titanium: Sapphire Laser as an Excitation Source In Two-Photon Spectroscopy" Applied Spectroscopy, vol. 51, No. 2, pp. 218-226 (1997).

Sun-Yung Chen, et al. "Theory of two-photon induced fluorescence anisotropy decay in membranes" Biophys. J. Biophysical Society, vol. 64, pp. 1567-1575 (May 1993).

Joseph R. Lakowicz, et al. "Two-Color Two-Photon Excitation of Fluorescence" Photochemistry and Photobiology, pp. 632-635 (1996).

George C. Nieman, et al. "A new electronic state of ammonia observed by multiphoton ionization", J. Chem. Phys. 68(12) pp. 5656-5657 (1978).

Philip M. Johnson, "The multiphoton ionization spectrum of benzene" Journal of Chemical Physics, vol. 64, No. 10, 4143-4148 (May 1976).

P.M. Johnson, et al. "The Discovery of a 3p Rydberg State in Benzene By Three-Photon Resonant Multiphoton Ionization Spectroscopy" Chemical Physics Letters, pp. 53-56 (1983).

S.G. Grubb, et al. "The three-photon spectrum of the $^1B_{2u}$—$^1A_{1g}$ transition in benzene: Analysis of vibronic and rotational structure" J. Chem. Phys. 81 (12), American Institute of Physics, pp. 5255-5265 (1984).

J.R. Cable, et al. "A condensed phase study of the benzene $B_{2u}$—$^1A_{1g}$ three-photon transition" J. Chem. Phys. 85 (6), American Institute of Physics, pp. 3155-3164 (1986).

Philip M. Johnson, "The multiphoton ionization spectrum of trans-1,3 butadiene" Journal of Chem. Physics, vol. 64, No. 11, pp. 4638-4644 (1976).

Mark Seaver, et al. "Double Resonance Multiphoton Ionization Studies of High Rydberg States in NO", J. Phys. Chem, 1983, 87, pp. 2226-2231. American Chemical Society.

Hammer, D.X., et. al., (1996) Experimental investigation of ultrashort pulse laser-induced breakdown thresholds in aqueous media. *Ieee J. Quant. Electron.* 3 2, 670-678.

Fisher, A.M.R., et. al., (1995) Clinical and Preclinical photodynamic theraphy. *Lasers Surg. Med..* 1 7, 2-31.

Draumer,N.H., et. al., (1997) Femtosecond dynamics of excited-state evolution in $(Ru(bpy)_3)^{2+}$. *Science* 2 7 5, 54-57.

Wilson, B.C. and M.S. Patterson, (1986) The physics of photodynamic therapy. *Phys. Med. Biol.* 3 1, 327-360.

Niemz, M.H., (1995) Theshold dependance of laser-induced optical breakdown on pulse duration. *Appl. Phys. Lett.* 6 6, 1181-1183.

Cheong, W.F., et. al., (1990) A review of the optical properties of biological tissues. *IEEE J. Quant. Electron.* 2 6, 2166-2185.

Dougherty, T.J., et. al., (1975) Photoradiation therapy II. Cure of animal tumors with hematoporphyrin and light. *J. Natl. Cancer Inst.* 5 5, 115-120.

Gomer, C.J., et. al., (1989) Properties and applications of photodynamic therapy. *Rad. Res.* 1 2 0, 1-18.

Kessel, D., et. al., (1991) Photophysical and photobiological properties of diporphyrin ethers. *Photochem. Photohio.* 5 3, 469-474.

Dolphin, D. (1994) 1993 Syntex award lecture, photomedicine therapy. *Can. J. Chem.* 7 2, 1005-1013.

Katsumi, T.A., et. al., (1996) Photodynamic therapy with a diode laser for implanted fibrosarcoma in mice Employing mom-L-aspartyl chlorin E6. *Photochem. Photohio.* 6 4, 671-675.

Gopert-Mayer, M., (1931) Elementary process with two quantum jumps. *Ann. Physik* 9, 273-294.

Kaiser, W. and C.G.B. Garrett, (1961) Two photon excitation in $CaF_2Eu^{2+}$. *Phys. Rev. Lett.* 7, 229-231.

Monson, P.R. and W.M. McClain, (1970) Polarization dependence of the two-photon absorption of tumbling molecules with application of liquid 1-chloronaphthalene and benzene, *J. Chem. Phys.* 5 3, 29-37.

Hermann, J.P. and J. Ducuing, (1972) Dispersion of the two-photon cross section in rhodamine dyes. *Opt. Comm.* 6, 101-105.

Denk, W., et. al., (1976) Two-photon molecular excitation in Laser-scannind and microscopy. *Handbook of Biological Confocal Microscopy, 2d Ed.*.(Ed. A.J.B. Pawley) 445-448. Plenum Press, New York.

Swofford, R.L. and W.M. McClain, (1975) The effect of spatial and temporal laser beam characteristics on two-photon absorption. *Chem. Phys. Lett.* 3 4, 455-459.

Georges, J., et. al., (1996) Limitations arising from optical saturation in fluorescence and thermal lens apectrometries using pulsed laser excitation: application to the . . . *Appl. Spectrose.* 5 0, 1505-1511.

Andreoni, A., et. al., (1982) Two-step laser activation of hematoporphyin derivative. *Chem. Phys. Lett.* 8 8, 37-39.

Shea, C.R., et. al., (1990) Mechanistic investigation of doxycyckine photosensitization by picosecondpulsed and sontinous wave laser irradiation of cells in culture. *J. Biol. Chem.* 2 6 5, 5977-5982.

Inaba, H., et. al., (1985) Nd: YAG laser-induced hematoporophyrin visible flourescence and two-photon-excited photochemical effect on malignant tumor cells. *J. Opt. Soc. Am. A: Opt. Image Science* 2, P72 (mtg. abstrc.).

Mashiko, S., et. al., (1986) Two-photon excited visible florescence of hematoporphyrin and phiophorbide-a and in vitro experiments of the photodynamic . . . *J. Opt. Soc. Am. B: Opt. Phys.* 3, p. 72-73 (mtg abstrc.).

Yamashita, Y., et. al., (1991) Photodynamic therapy using pheophorbide-a and Q-switched Nd: YAG laser on implanted human hepatocellular carcinoma. *Gast. Jap.* 2 6, 623-627.

Fugishima, I., et. al., (1991) Photodynamic therapy using phophorbide-a and Nd: YAG laser. *Neurol. Med. Chir.* (Tokyo) 3 1, 257-263.

Mashiko, S., et. al., (1985) Basic study on photochemical effect of pheophorbide-a irradiated by Nd: YAG laser light. *Nippon Laser Igakukaishi.* 6, 113-116.

Steil, H., et. al., (1993) Photophysical properties of the photosensitizer phophorbide a studied at high photon flux densities. *J. Photochem. Photobiol. B: Biology* 1 7, 181-186.

Bodaness, R.S. and D.S. King (1985) The two-photon induced fluorescence of the tumor localizing Photo-Sensitizer hematoporphyrin derivaties via 1064 nm . . . *Biochem. Biophys. Res. Comm.* 1 2 6, 346-351.

Bodaness, R.S. et al. (1986) The two-photon laser-induced fluorescence of the tumor-localizing photosensitive hematoporphyrin derivative. *J. Biol. Chem.* 2 6 1, 12098-12101.

Lenz, P., (1995) In vivo excitation of photosensitizers by infrared light. *Photochem. Photobio.* 6 2, 333-338.

Patrice, T., et. al., (1983) Neodymium-yttrium aluminum garnet laser destruction of nonsensitized and hematoporphyrin derivative-sensitized tumors. *Cance. Res.* 4 3, 2876-2879.

Marchesini, R., et. al., (1986) A study on the possible involvement of nonlinear mechanism of light absorption by HpD with Nd: YAG laser. *Lasers Surg. Med.* 6, 323-327.

Oh, D.H., et. al., (1997) Two-photon excitation of 4-hydroxymenthy1-5,5' ,8-trimethylpsoralen. *Photochem. Photobio.* 6 5, 91-95.

Prasad, P.N. and G.S. He, (1996) Multiphoton resonant non-linear-optical processes in organic molecules. *ACS Symposium Series* 6 2 8, 225-236.

Dagani, R., (1996) Two photons shine in 3-D data storage. *Chem Eng. News* Sep. 23, 1996, 68-70.

Lytle, E.E., (1981) Laser Fundamentals. *Lasers in Chem Analysis* (Ed. G.M. Hieftjie, et. al.), 5-6 The humana Press, New Jersey.

Song, P.S. and K.J. Tapley Jr., (1979) Photochemistry and photobiology of psoralens *Photochem. Photobio.* 2 9, 1177-1197.

Spence, D.E>, et. al., (1991) 60-fsee pulse generation from a self-mode-locked TEsapphire laser. *Opt. Lett.* 1 6, 42-44.

Cimino, G.D., et. al., (1985) Psoralens as photoactive probes of nucleic acid structure and function: organic chemistry, photochemistry, and biochemistry. *Ann. Rev. Biochem.* 5 4, 1151-1193.

Fisher, W.G., et. al., (1997) Two photon spectroscopy and photochemistry of tris (2,2'-bipyridine)—ruthenium(II). *J. Phys. Chem.* (In-press).

Moscatelli, E.A., (1985) A simple conceputal mpde; for two-photon absorption. *Am. J. Phys.* 5 4, 52-54.

Fisher, W.G., et. al., (1997) The titanium sapphire laser as an excitation source in two-photon spectroscopy. *Appl. Spectrose.* 5 1, (In press).

Lytle, E.E., et. al., (1980) Two-photon excitation spectra of polycyclic aromatic hydrocarbons. *Intern. J. Environ. Anal. Chem.* 8, 303-312.

Peticolas, W.L., (1967) Multiphoton spectroscopy. *Ann. Rev. Phys. Chem.* 1 8, 233-260.

McClain, W.M. (1974) Two-photon molecular spectroscopy. *Acc. Chem. Res.* 7, 129-135.

McClain, W.M., (1971) Excited state symmetry assignment through polarized two-photon absorption studies of fluids. *J. Chem. Phys.* 5 5, 2789-2796.

Freeman, R.G., et. al., (1990) Second harmonic detection of sinusoidally modulated two-photon excited flourescence. *Anal. Chem.* 6 2, 2216-2219.

Fisher, W.G., et. al. (1993) Second harmonic detection of spatially filtered two-photon excited fluroscence. *Anal. Chem.* 6 5, 631-635.

Kennedy, S.M. and E.E. Lytle, (1896) p-Bis(o-methylstyryl) benezene as a power-squared sensor for two-photon absorption measeurement between 537 and 694 nm. *Anal. Chem.* 5 8, 2643-2647.

Chan, C.K. and S.O. Sari, (1974) Tunable dye laser pulse converter for production of picosecond pulses. *Appl. Phys. Lett.* 2 5, 403-406.

Harris, J.M., et. al., (1975) Pulse generation in cw-dye laser by mode-locked synchronous pumping. *Appl. Phys. Lett.* 2 6, 16-18.

Vo-Dinh, et.al., (1995) In Vivo Cancer Diagnosis of the Esophagus Using Differential Normalized Fluorescence (DNF) Indices, *Lasers in SUrgery and Medicine*, 16: 41-47.

Panjehpour, et. al., (1995) Spectroscopic Diagnosis of Esophageal Cancer: New Classification Model, Improved Measurement System, *Gastroinestinal Endoscopy*, 41(6): 577-581.

Wirth, et. al., (1977) Two-photon Excited Molecular Fluorescence in Optically Dense Media, *Anal. Chem.* 49(13): 2054-2057.

Wirth, et. al., (1990) Very High Detectability in Two-Photon Spectroscopy, *Anal. Chem*, 62(9): 973-976.

Denk, et. al., (1995) Two-Photon Molecular Excitation in Laser Scanning Microscopy, *Handbook of Bio. Confocal Microscopy, 2d ed.*, Plenum Press, New York, 445-458.

Freeman, et. al., Second Harmonic Detection of Sinusoidally Modulated Two-Photon Excited Fluorescence. *Anal. Chem.*, 62(20): 2216-2219.

Fisher, et. al., (1993) Second Harmonic Detection of SPatially Filetered Two-Photon Excited Fluroescence, *Anal. Chem*, 65(5): 631-635.

* cited by examiner

METHODS FOR IMPROVED SELECTIVITY IN PHOTO-ACTIVATION AND DETECTION OF MOLECULAR DIAGNOSTIC AGENTS

This application is a divisional of U.S. application Ser. No. 08/741,370, filed on Oct. 30, 1996 now U.S. Pat. No. 5,832,931.

This invention was made with Government support under Contract No. DE-AC05-84OR21400 awarded by the U.S. Department of Energy to Lockheed Martin Energy Systems, Inc. Lockheed Martin Energy Systems and the Oak Ridge Associated Universities have waived rights to this invention to the inventors. The Government has rights in this invention pursuant to Contract No. DE-AC05-84OR21400 awarded by the U.S. Department of Energy.

BACKGROUND OF THE INVENTION

1. Field of the Invention

The present invention relates generally to methods and apparatus for remotely effecting spatially-selective photo-activation of one or more molecular agents and for improving the detection of the diagnostic signals thereby produced. The method taught for effecting photoactivation utilizes the special properties of non-linear optical excitation for promoting an agent from one molecular energy level to another with a high degree of spatial and molecular specificity. The special features of this method are applicable for activation of various endogenous and exogenous imaging agents, and in particular afford distinct advantages in the diagnosis of diseases in humans and animals. Specifically, use of non-linear excitation methods facilitate controlled activation of diagnostic agents in deep tissue using near infrared to infrared radiation, which is absorbed and scattered to a lesser extent than methods and radiations currently used. Combination of these non-linear excitation methods with advanced signal encoding and processing methods greatly increases sensitivity in the detection of diagnostic signals.

2. Description of the Prior Art

An urgent need exists in many fields, and especially in the medical diagnostics field, for a method that is capable of selectively controlling the remote activation of various molecular agents while producing few if any side effects resulting from the activation process. The desired improvements in activation include enhancements in spatial or temporal control over the location and depth of activation, reduction in undesirable activation of other co-located or proximal molecular agents or structures, and increased preference in the activation of desirable molecular agents over that of undesirable molecular agents. Various linear and non-linear optical methods have been developed to provide some such improvements for some such agents under very specialized conditions. However, in general the performance and applicability of these methods have been less than desired. Specifically, improved photo-activation methods are needed that may be used to selectively photo-activate a variety of molecular diagnostic agents while providing improved performance in the control of application of this photo-activation.

Application of optical radiation as a means for remotely activating molecular probes has been known for many years. Specifically, linear optical excitation methods have been used extensively as a means for achieving semi-selective activation of molecular diagnostic agents. Linear optical excitation occurs when a target agent, such as a molecular diagnostic agent, undergoes a specific photo-chemical or photo-physical process, such as fluorescent emission, upon absorption of energy provided by a single photon. These processes can in many cases be very efficient, and use of such processes is attractive for numerous applications. Unfortunately, performance of these linear methods have not always been as successful as desired. For example, there is strong evidence that ultraviolet radiation used to excite some molecular probes can produce disease in humans and animals, such as induced skin cancer, along with other undesirable side effects. Furthermore, a less than desirable penetration depth has plagued most efforts at linear optical excitation of molecular agents, primarily as a consequence of the effects of optical scatter and of absorbance of the incident probe radiation at wavelengths near the linear absorption bands of these agents. As an example, Wachter and Fisher (E. A. Wachter and W. G. Fisher, "Method and Apparatus for Evaluating Structural Weakness in Polymer Matrix Composites," U.S. Pat. No. 5,483,338) teach of a rapid optical method capable of sensitively imaging chemical transformations in probe molecular agents; however, due to scatter and absorbance of the incident probe radiation, the method is only suitable for topical analysis. Vo-Dinh and co-workers (T. Vo-Dinh, M. Panjehpour, B. F. Overholt, C. Farris, F. P. Buckley III and R. Sneed, "In-Vivo Cancer-Diagnosis of the Esophaous Using Differential Normalized Fluorescence (Dnf) Indexes," Lasers in Surgery and Medicine, 16 (1995) 41-47; and M. Panjehpour, B. F. Overholt, J. L. Schmidhammer, C. Farris, P. F. Buckley, and T. Vo-Dinh, "Spectroscopic Diagnosis of Esophageal Cancer: New Classification Model, Improved Measurement System," Gastrointestinal Endoscopy, 41 (1995) 577-581) teach of the use of similar linear optical probe methods for detection of diseased tissues in humans; however, this approach is also plagued by less than desirable penetration depth and is limited to detection of superficial lesions due to scatter and absorption of the incident probe radiation. Also, because this type of excitation is linearly related to excitation power, such methods provide no effective means for limiting the location of probe excitation along the optical path. In fact, virtually all examples of the use of linear optical excitation are plagued by fundamental performance limits that are attributable to undesirable absorption and scatter of the incident optical radiation by the surrounding matrix, poor specificity in excitation of probe molecular species, and a lack of suitable physical mechanisms for precise control of the extent and depth of activation.

Various non-linear optical excitation methods have been employed in an effort to achieve specific improvements in the selectivity of photo-activation for certain applications, and to address many of the limitations posed by linear excitation methods. In fact, the non-linear process consisting of simultaneous absorption of two photons of light by a molecule to effect excitation equivalent to that resulting from absorption of a single photon having twice the energy of these two photons is very well known, as are the specific advantages of this process in terms of reduced absorption and scatter of excitation photons by the matrix, enhanced spatial control over the region of excitation, and reduced potential for photo-chemical and photo-physical damage to the sample. Excitation sources ranging from single-mode, continuous wave (CW) lasers to pulsed Q-switched lasers having peak powers in excess of 1 GW have been employed for numerous examples of two-photon excitation methods. For example, Wirth and Lytle (M. J. Wirth and F. E. Lytle, "Two-Photon Excited Molecular Fluorescence in Optically Dense Media," Analytical Chemistry, 49 (1977) 2054-2057) teach use of non-linear optical excitation as a means for stimulating target molecules present in optically dense media; this method is shown to be useful in limiting undesirable direct interaction of the probe radiation with the media itself, and provides a means for effectively exciting target molecular agents present in strongly absorbing or scattering matrices. Improved spatial control over the active region has been further developed by Wirth (M. J. Wirth and H. O. Fatunmbi, "Very High Detectability in Two-Photon Spectroscopy," Analytical Chemistry, 62 (1990) 973-976); specifically, Wirth teaches a method for achieving extremely high spatial selectivity in the excitation of target molecular agents using a microscopic imaging system. Similar control has been further applied by Denk et al. (W. Denk, J. P. Strickler and W. W. Webb, "Two-Photon Laser Microscopy," U.S. Pat. No. 5,034,613) who teach of a special epi-illumination confocal laser scanning microscope utilizing non-linear laser excitation to achieve intrinsically high three-dimensional control in the photo-activation of various molecular fluorophor agents on a cellular or sub-cellular scale. This microscope is used to excite molecular fluorophor agents added to biological specimens, which constitute an optically dense medium; the special properties of non-linear two-photon excitation are utilized to substantially limit excitation and subsequent detection of the fluorescent signal thus produced to a confocal region occurring at the focus of an objective lens, thereby enhancing contrast in three-dimensional imaging by sharply controlling the depth of focus. Emitted fluorescent light is collected by the excitation objective using an epi-illumination configuration. Control of photo-excitation for generation of luminescence-based images at the cellular and subcellular level is shown in target samples mounted on a stage. Furthermore, Denk teaches that reduction in photo-induced necrosis of cells located at the focal plane is a primary benefit of this microscopy approach, based on the replacement of ultraviolet excitation radiation with less damaging near infrared excitation radiation.

In later work by Denk et al. (W. Denk, D. W. Piston and W. W. Webb, "Two-Photon Molecular Excitation in Laser-Scanning Microscopy," in Handbook of Biological Confocal Microscopy, Second Edition, J. B. Pawley, ed., Plenum Press, New York, 1995, pp. 445-458) an external whole area detection method is taught for collection of microscopic imaging data produced from two-photon excited fluorescent tags. This method, which the authors state as being "as yet untried," eliminates the need to collect backscattered fluorescent light using epi-illumination (see p. 452). Denk points out that this approach could be useful if the microscope objective does not transmit the emitted fluorescent wavelengths, but that it is "vulnerable to contamination from ambient room light." In this work and in the earlier Denk patent (U.S. Pat. No. 5,034,613), no apparent method is used or anticipated for reduction of background interference from either ambient light or from scattered excitation light.

In fact, the well known low efficiency of the two-photon excitation process can translate into a very high ratio of scattered, unabsorbed excitation light to fluorescence emission. Use of various modulation methods for reduction of interference from scattered excitation light, as well as from interferences from ambient light and from other environmental and instrumental background sources, has numerous precedents. In the field of two-photon excited fluorescence, Lytle and co-workers (R. G. Freeman, D. L. Gilliland and F. E. Lytle, "Second Harmonic Detection of Sinusoidally Modulated Two-Photon Excited Fluorescence," Analytical Chemistry, 62 (1990) 2216-2219; and W. G. Fisher and F. E. Lytle, "Second Harmonic Detection of Spatially Filtered Two-Photon Excited Fluorescence," Analytical Chemistry, 65 (1993) 631-635) teach sophisticated methods for rejection of scattered laser excitation light by making use of second-harmonic detection methods: when sinusoidal modulation of the excitation light is performed at one frequency, and detection of the two-photon excited fluorescence is performed at twice that frequency (which is the second harmonic of the excitation modulation frequency), interferences from scattered excitation light are virtually eliminated. And by proper selection of the modulation frequency to avoid electronic and other noise frequencies, rejection of instrumental and environmental interferences is extremely high.

Hence, it is well known that two-photon excitation of fluorescence can be used under laboratory conditions to excite molecular fluorophors using light at approximately twice the wavelength of that used for linear single-photon excitation, and that the excitation thereby effected can improve three-dimensional spatial control over the location of excitation, can reduce interference from absorption and scatter of the excitation light in optically dense media, and can reduce collateral damage along the excitation path to living cell samples undergoing microscopic examination.

Nonetheless, while the substantial body of prior art exemplified by these cited examples clearly demonstrates many attractive features of various photo-activation methods that are applicable for diagnostic and other in vivo microscopic imaging uses, a general method for achieving selective photo-activation of one or more molecular agents with a high degree of spatial control that is capable of meeting the diverse needs of the medical diagnostic industry has not been previously taught. Specifically, practical methods for effecting such control on scales that are significant for medical diagnostic applications have not been previously taught.

It is, therefore, an object of the present invention to provide a general method for achieving selective photo-activation of one or more molecular agents with a high degree of spatial control.

It is another object of the present invention to provide such a method that is capable of meeting the diverse needs of the medical diagnostic industry.

It is another object of the present invention to provide a practical method for effecting such control on scales that are significant for medical diagnostic applications.

SUMMARY OF THE INVENTION

Having regard to the above and other objects and advantages, the present invention generally provides for a method for the imaging of a particular volume of plant or animal tissue, wherein the plant or animal tissue contains at least one photo-active molecular agent. The method comprises the steps of treating the particular volume of the plant or animal tissue with light sufficient to promote a simultaneous two-photon excitation of the photo-active molecular agent contained in the particular volume of the plant or animal tissue, photo-activating at least one of the at least one photo-active molecular agent in the particular volume of the plant or animal tissue, thereby producing at least one photo-activated molecular agent, wherein the at least one photo-activated molecular agent emits energy, detecting the energy emitted by the at least one photo-activated molecular agent, and producing a detected energy signal which is characteristic of the particular volume of plant or animal tissue. The present invention also provides a method for the imaging of a particular volume of material, wherein the material contains at least one photo-active molecular agent.

In a preferred embodiment of the present invention, the light sufficient to promote a simultaneous two-photon excitation of the at least one photo-active molecular agent is laser light. It is also preferred that the light sufficient to promote a simultaneous two-photon excitation of the photo-active molecular agent is a focused beam of light, and more preferred that the focused beam of light is focused laser light.

Another preferred embodiment of the present invention further includes a first step of treating the material, plant tissue or animal tissue with at least one photo-active molecular agent, wherein the particular volume of the material, plant tissue or animal tissue retains at least a portion of the at least one photo-active molecular agent. It is more preferred that the at least one photo-active molecular agent is selected from the group consisting of psoralen, 5-methoxypsoralen (5-MOP), 8-methoxypsoralen (8-MOP), 4,5',8-trimethylpsoralen (TMP), 4'-aminomethyl-4,5',8-trimethylpsoralen (AMT), 5-chloromethyl-g-methoxypsoralen (HMT), angelicin (isopsoralen), 5-methylangelicin (5-MIP), 3-carboxypsoralen, porphyrin, haematoporphyrin derivative (HPD), photofrin II, benzoporphyrin derivative (BPD), protoporphyrin IX (PpIX), dye haematoporphyrin ether (DHE), polyhaematoporphyrin esters (PHE), 13,17-N,N,N-dimethylethylethanolamine ester of protoporphyrin (PH1008), tetra (3-hydroxyphenyl)-porphyrin (3-THPP), tetraphenylporphyrin monosulfonate (TPPS1), tetraphenylporphyrin disulfonate (TPPS2a), dihaematoporphyrin ether, mesotetraphenylporphyrin, mesotetra(4N-methylpyridyl)porphyrin (T4 MpyP), octa-(4-tert-butylphenyl)tetrapyrazinoporphyrazine (OPTP), phthalocyanine, tetra-(4-tert-butyl)phthalocyanine ($t_4$-$PcH_2$), tetra-(4-tert-butyl)phthalocyanato-magnesium ($t_4$-PcMg), chloroaluminum sulfonated phthalocyanine (CASPc), chloroaluminum phthalocyanine tetrasulfate (AlPcTS), mono-sulfonated aluminum phthalocyanine (AlSPc), di-sulfonated aluminum phthalocyanine (AlS2Pc), tri-sulfonated aluminum phthalocyanine (AlS3Pc), tetra-sulfonated aluminum phthalocyanine (AlS4Pc), silicon phthalocyanine (SiPc IV), zinc II phthalocyanine (ZnPc), bis(di-isobutyl octadecylsiloxy)silicon 2,3-naphthalocyanine (isoBOSINC), germanium IV octabutoxyphthalo-cyanine (GePc), rhodamine 101 (Rh-101), rhodamine 110 (Rh-110), rhodamine 123 (Rh-123), rhodamine 19 (Rh-19), rhodamine 560 (Rh-560), rhodamine 575 (Rh-575), rhodamine 590 (Rh-590), rhodamine 610 (Rh-610), rhodamine 640 (Rh-640), rhodamine 6G (Rh-6G), rhodamine 700 (Rh-700), rhodamine 800 (Rh-800), rhodamine B (Rh-B), sulforhodamine 101, sulfo-rhodamine 640, sulforhodamine B, coumarin 1, coumarin 2, coumarin 4, coumarin 6, coumarin 6H, coumarin 7, coumarin 30, coumarin 47, coumarin 102, coumarin 106, coumarin 120, coumarin 151, coumarin 152, coumarin 152A, coumarin 153, coumarin 311, coumarin 307, coumarin 314, coumarin 334, coumarin 337, coumarin 343, coumarin 440, coumarin 450, coumarin 456, coumarin 460, coumarin 461, coumarin 466, coumarin 478, coumarin 480, coumarin 481, coumarin 485, coumarin 490, coumarin 500, coumarin 503, coumarin 504, coumarin 510, coumarin 515, coumarin 519, coumarin 521, coumarin 522, coumarin 523, coumarin 535, coumarin 540, coumarin 540A, coumarin 548, 5-ethylamino-9-diethylamino-benzo[a]phenoxazinium (EtNBA), 5-ethyl-amino-9-diethyl-aminobenzo[a]phenothiazinium (EtNBS), 5-ethylamino-9-diethylaminobenzo[a]pheno-selenazinium (EtNBSe), chlorpromazine, chlorpromazine derivatives, chlorophyll derivatives, bacteriochlorophyll derivatives, metal-ligand complexes, tris(2,2'-bipyridine)ruthenium (II) dichloride (RuBPY), tris(2,2'-bipyridine)rhodium (II) dichloride (RhBPY), tris(2,2'-bipyridine)platinum (II) dichloride (PtBPY), pheophorbide a, merocyanine 540, vitamin D, 5-amino-laevulinic acid, photosan, chlorin e6, chlorin e6 ethylene-diamide, mono-L-aspartyl chlorin e6, and phenoxazine Nile blue derivatives, stilbene, stilbene derivatives, and 4(N-(2-hydroxyethyl)-N-methyl)-aminophenyl)-4'-(6-hydroxyhexylsulfonyl)-stilbene (APSS). It is also more preferred that the at least one photo-active molecular agent is at least one biogenic photo-active molecular agent that is specific to a particular material or tissue within the particular volume of material, plant tissue or animal tissue, even more preferred that the at least one biogenic photo-active molecular agent includes a segment selected from the group consisting of DNA, RNA, amino acids, proteins, antibodies, ligands, haptens, carbohydrate receptors or complexing agents, lipid receptors or complexing agents, protein receptors or complexing agents, chelators, and encapsulating vehicles and yet further more preferred that the at least one biogenic photo-active molecular agent further includes a segment which is photo-activated when subject to light sufficient to promote a simultaneous two-photon excitation.

In yet another preferred embodiment of the present invention, the step of treating the particular volume of the material, plant tissue or animal tissue with light sufficient to promote a simultaneous two-photon excitation of the at least one photo-active molecular agent contained in the particular volume of the material, plant tissue or animal tissue further includes the step of modulating light from a light source with a particular type of modulation, thereby producing a modulated light, and the step of treating the particular volume of the material, plant tissue or animal tissue with the modulated light sufficient to promote a simultaneous two-photon excitation of the at least one photo-active molecular agent contained in the particular volume of the material, plant tissue or animal tissue. It is also preferred that the present invention further include the steps of demodulating the detected energy signal with the particular type of modulation, and producing a demodulated energy signal which is characteristic of the particular volume of the material, plant tissue or animal tissue.

It is more preferred that the step of detected the energy signal with the particular type of modulation includes demodulating the detected energy signal at a frequency twice that of the particular type of modulation, thereby detecting the second harmonic of the particular type of modulation. It is also more preferred that the demodulated energy signal which is characteristic of the particular volume of the material, plant tissue or animal tissue represents a change in lifetime of at least one photo-activated molecular agent present in the particular volume of the material, plant tissue or animal tissue.

BRIEF DESCRIPTION OF THE DRAWINGS

The above and other features and advantages of the invention will become further known from the following detailed description of preferred embodiments of the invention in conjunction with the drawings in which.

DETAILED DESCRIPTION OF THE DRAWINGS

Figure 1:
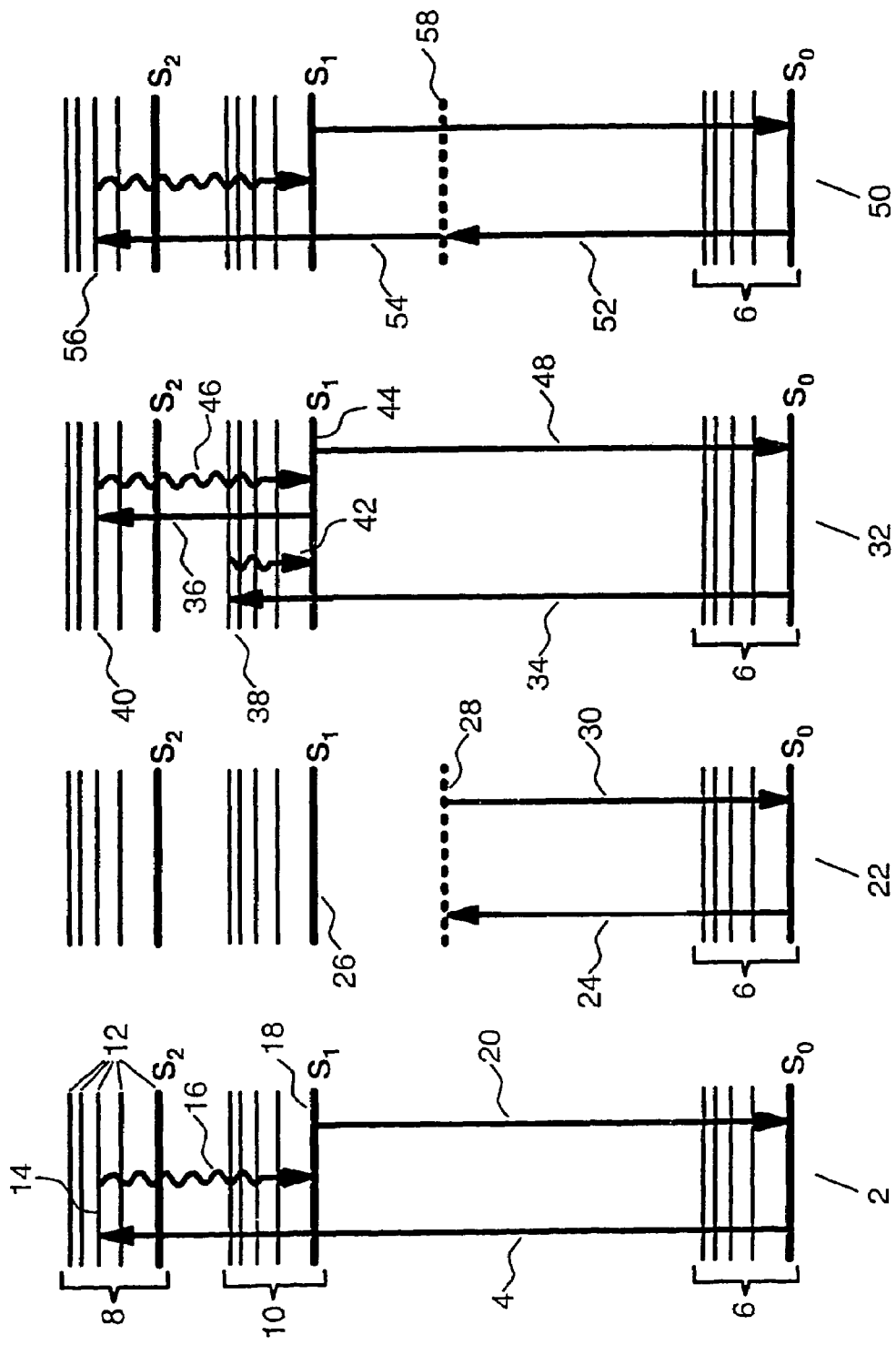
FIG. 1 shows example energy level diagrams for linear and non-linear optical excitation.

The invention described here utilizes the unique physical properties of non-linear optical excitation of molecular agents to effect improved spatial control over the photo-activation of those agents. In addition, non-linear optical excitation is shown to have further advantages during photo-activation of medical diagnostic and other agents, including reduction of collateral excitation and damage along the excitation path, reduction in exposure to harmful optical wavelengths, and reduction of interference from absorption and scattering processes originating from the environment surrounding the excited agent.

The fundamental significance of the invention taught in this disclosure lies in the use of non-linear, simultaneous two-photon optical excitation processes to remotely photo-activate one or more molecular diagnostic agent with a high degree of spatial control and improved depth of penetration. These molecular agents may be exogenous agents added to the system under examination, or they may be endogenous components of the system. Example exogenous diagnostic agents include various psoralen derivatives, while example endogenous agents include aromatic amino acids and nucleic acids. Two-photon excitation is performed at a wavelength approximately twice that of corresponding single-photon absorbance bands. By focussing a beam of optical radiation into a specimen under examination, the diagnostic agent may be excited at a location substantially limited to the confocal region of the focussed beam. The confocal region, $Z_c$, is defined as the zone extending a distance of $2\pi\ w_0^2/\lambda$, where $w_0$ is the diameter of the minimum beam waist and $\lambda$ is the wavelength of the optical radiation. In contrast, when linear excitation methods are employed, excitation occurs substantially along the entire optical path, making spatial localization of excitation considerably less defined. Thus, use of the two-photon excitation process greatly increases the resolution of excitation alone the optical path. Further, since excitation is performed at long wavelengths relative to corresponding linear excitation processes, scatter and absorption of the excitation energy is greatly reduced. For thick, optically dense samples, such as human tissue, this means that two-photon excitation is possible at depths considerably greater than is possible using linear excitation methods. It is not necessary for the light emitted from the diagnostic agent to be detected or imaged directly without scatter, since spatial information concerning the origin of the emitted light is encoded by and may be correlated to do the excitation focus. By moving the location of this focus relative to the specimen, a two- or three-dimensional image of the emitted light may be developed. Also, by modulating the excitation light and using an appropriate demodulation method on the detection apparatus, rejection of scattered excitation light and other interferences may be markedly improved.

The present invention is intended primarily for in vivo detection and imaging of disease and other characteristics of tissues, such as cancer in the human breast. However, it will be clear once the invention is fully disclosed that the methods and apparatus taught have numerous additional applications, and that these methods and apparatus can be applied to the field of two-photon laser scanning microscopy, as taught by Denk et al., to achieve substantive improvements in the performance characteristics of such instruments. To begin this full disclosure, a review of the fundamental physics underlying linear and non-linear optical excitation will be useful.

Comparison of Linear and Non-Linear Excitation—Energy Level Diagram Formulation:

FIG. 1 shows typical molecular energy level diagrams for several linear and non-linear optical excitation processes. In this representation, which consists of simplified Jablonski diagrams, the vertical direction corresponds to a change in energy, while the horizontal direction represents the sequence of events, progressing from the left to right. Solid horizontal lines represent quantum mechanically allowed molecular energy levels, while dashed horizontal lines represent disallowed, virtual energy levels. Quantum mechanically allowed molecular energy levels are relatively long lived and the probability of excitation of a molecule upon absorption of energy, such as that provided by absorption of a photon of appropriate energy, is high. Virtual energy levels may be reached through a variety of excitation processes, but in contrast to allowed molecular transitions they have exceedingly short lifetimes (on the order of $10^{-15}$ s, as predicted by the Heisenberg uncertainty principle), making them significant only under special excitation conditions. Straight arrows in Jablonski diagrams represent radiative energy transfer processes: upward arrows indicate absorption of energy, while downward arrows represent radiative emission, such as fluorescent or phosphorescent emission of a photon. Crooked arrows represent non-radiative energy transfer processes, such as vibrational relaxation. The vertical length of the straight or crooked arrows is proportional to energy absorbed or emitted in a given process.

For the first Jablonski diagram shown in FIG. 1, single-photon excitation to an allowed energy level 2 occurs upon absorption of a photon 4 having sufficient energy to directly promote the molecule from a first allowed electronic energy level 6 (generally the lowest electronic energy level, or ground state, denoted as $S_0$) to a second allowed electronic energy level 8 having a higher overall energy level (represented here as the $S_1$ state). Note that there may be multiple allowed higher electronic energy levels to which excitation may occur, and that these are typically denoted $S_1$, $S_2$, and so on as their energy increases. The nomenclature $S_1$ indicates a singlet electronic energy level that conforms to the Pauli exclusion principle, wherein the spins of all electrons are paired and these paired electron spins are opposite to one another. One or more triplet excited states 10 may also be possible for some molecular systems, with the example here denoted as $T_1$. Triplet states differ from singlet states in that the spins of all electrons are paired except for two. Each allowed electronic energy level (singlet or triplet) may be further subdivided into an ensemble of discrete vibrational levels 12; each of these discrete vibrational levels 12 may in turn be further subdivided into an ensemble of discrete rotational energy levels. Hence, each allowed electronic energy level, $S_0$, $S_1$, $T_1$, and so on, constitutes a complex band of allowed energy levels due to the large number of possible vibrational and rotational states possible. Upon absorption of energy from a photon 4 the molecule is promoted to a particular unique electronic and vibrational level 14, sometimes referred to as a vibronic level. From this excited state the molecule can then undergo rapid internal conversion 16, for example to the lowest allowed excited vibronic energy level 18 in the second allowed electronic energy level 8. This internal conversion 16 is typically very fast, occurring on a time scale on the order of $10^{-12}$ to $10^{-15}$ sec. Finally, the excited molecule can undergo further relaxation, such as through collisional deactivation 20, to return to the initial, first energy level 6. Alternative relaxation processes include fluorescent emission of a photon 21, which occurs directly from $S_1$ to $S_0$, and phosphorescence, which occur following intersystem crossing 22 from a singlet state to a triplet state 10. Note that singlet to singlet electronic transitions, such as those shown for $S_1 \rightarrow S_0$, constitute quantum mechanically allowed transitions according to the Pauli exclusion principle. In contrast, transitions from a singlet to a triplet state 10, such as $S_1 \rightarrow T_1$, are quantum mechanically forbidden since the electron spins do not remain paired. However, the probability of internal conversion is greater than zero for some molecular systems as a consequence of the relatively long lifetime of the $S_1$ state compared to the intersystem crossing rate constant for these systems. Transition from the triplet state 10 back to a singlet state, such as $T_1 \rightarrow S_0$, can occur via the radiative process known as phosphorescent emission of a photon 24. Phosphorescence is generally characterized by a relatively long radiative lifetime compared to fluorescence due to the disallowed nature of the process. An example of single-photon excitation to an allowed energy level 2 is promotion of the dye molecule coumarin from a ground electronic state to an excited electronic state through the absorption of a single photon 4 at 400 nm, followed by internal conversion 16 and subsequent fluorescent emission of a photon 21 at 480 nm. In this example the probability of excitation is linearly related to the power of the incident optical radiation, thus single-photon excitation to an allowed energy level 2 is referred to as a linear excitation process.

For the second Jablonski diagram shown in FIG. 1, single-photon excitation to a virtual energy level 26 occurs upon absorption of a photon 28 having insufficient energy to directly promote the molecule to a higher allowed electronic energy level 8. Instead, the molecule is promoted to a very short lived virtual energy level 30. This virtual energy level 30 will typically have a lifetime on the order of $10^{-15}$ sec. Virtually instantaneous re-emission 32 of the absorbed photon 28 from this virtual level 30 will typically occur via processes such as elastic scatter. An important example of this process is Rayleigh scatter at 800 nm from coumarin upon excitation with light at 800 nm. Another example is Raman scatter, which occurs when the molecule returns to the various vibrational levels associated with the ground state. In these example processes the probability of excitation is also linearly related to the power of the incident optical radiation, thus single-photon excitation to a virtual energy level 26 is also referred to as a linear excitation process.

For the final Jablonski diagram shown in FIG. 1, simultaneous two-photon excitation to an allowed energy level 34 occurs upon simultaneous absorption of a first of two photons 36 and a second of two photons 38. In this case the combined energy of the first of two photons 36 and the second of two photons 38 is sufficient to promote the molecule from a first allowed energy level 6 to a second allowed energy level 8. Typically, the individual energies of neither the first of two photons 36 nor the second of two photons 38 is sufficient to directly promote this or any other allowed electronic transition. Instead, the first of two photons 36 promotes the molecule to a very short lived virtual energy level 30. This is the same virtual energy level as that shown in the second Jablonski diagram. Before re-emission 32 can occur from the virtual energy level 30, the second of two photons 38 immediately promotes the molecule to a second allowed electronic energy level 8. The result is excitation that is equivalent to that achieved using linear signal-photon excitation to an allowed energy level 2. Note that the first of two photons 36 and the second of two photons 38 may be of equal or unequal energy. Also, the instantaneous irradiance, or W m$^{-2}$, of the incident excitation light must be relatively high to yield significant efficiency in absorption of the second of two photons 38 before the virtual energy level 30 undergoes relaxation 32 back to the original first allowed electronic energy level 6. In fact, because the lifetime of the virtual energy level 30 is on the order of $10^{-15}$ sec, pulsed excitation sources having very high peak powers are commonly used to efficiently stimulate these processes; such sources are often preferable since they are capable of providing large numbers of photons to the excited molecule during the brief lifetime of the virtual energy level 30. Once the molecule has been promoted to the second allowed electronic energy level 8, it can then undergo rapid internal conversion 16, followed by further relaxation, such as through collisional deactivation 20, fluorescent emission of a photon 21, or intersystem crossing 22 to a triplet state 10. In the last case, transition from the triplet state 10 back to the singlet ground state 6, can occur via phosphorescent emission of a photon 24. It is notable that simultaneous two-photon excitation shares features of both single-photon excitation to an allowed energy level 2 and single-photon excitation to a virtual energy level 26, specifically in that a virtual energy level 30 plays a key role in the promotion of the molecule from the ground state to the excited state, and that once promoted to an excited energy level the molecule can undergo photo-chemical and photo-physical processes that are identical to those resulting from single-photon excitation to an allowed energy level 2. An example of the simultaneous two-photon excitation process is the promotion of the dye molecule coumarin from a ground electronic state to an excited electronic state through the simultaneous absorption of two photons at 800 nm, followed by emission of a fluorescent photon at 480 nm. Due to the well known quadratic dependence on instantaneous photon irradiance, simultaneous two-photon excitation to an allowed energy level 50 is also referred to as a non-linear excitation process. The significant differences between linear and non-linear excitation processes are identified in the next section.

Note that in addition to the example energy level diagrams shown in FIG. 1, many other possible transitions and energy level conditions are possible, depending upon numerous factors, including the characteristics of the molecular system, its environment, and the particular energies of the absorbed and released forms of energy, along with their temporal and spatial correlations. Once a molecule has been promoted to an excited state, a variety of physical or chemical processes may occur, including luminescent emission of a photon, photochemical transformation, such as isomerization or oxidation, or photo-ionization. Importantly, though, it is the fundamental properties of the excited state and its environment that determine the ultimate fate of the molecule. Once excited, the mechanism responsible for promoting the molecule to the excited state has no significant impact on this fate since the excitation process itself does not directly impact the subsequent properties of the excited molecule or its environment. Hence, a molecular diagnostic agent that works well under single-photon excitation conditions may be expected to exhibit similar behavior under two-photon excitation conditions.

Comparison of Linear and Non-Linear Excitation—Power Dependence and Spatial Effects:

When light interacts with a molecular system, it induces a polarization that is proportional to the linear susceptibility multiplied by the magnitude of the applied electric field. When this electric field is very intense, the system cannot be described as easily, and higher order interaction terms must be included in the description of the induced polarization. Simultaneous two-photon excitation is referred to as a non-linear process because it occurs when the electromagnetic fields from two photons combine via these higher order terms, specifically the imaginary portion of the third-order susceptibility, $\chi^{(3)\prime\prime}$, to induce an electronic transition. This is another way of describing the non-linearity of simultaneous two-photon absorption. That is, the molecular system is reacting non-linearly to the intense electromagnetic field. In contrast, single-photon excitation processes may be described by the linear susceptibility and are linear with excitation power. Note that the cross-section for simultaneous two-photon excitation is typically about one hundred thousand-fold smaller than that for an equivalent single-photon excitation process. This is due to the low probability that two photons will simultaneously interact with a molecule during the lifetime of the extremely brief virtual energy level. However, the availability of optical excitation sources capable of providing extremely high peak powers, such as mode-locked lasers, can substantially ameliorate the impact of this low efficiency by increasing instantaneous incident powers and thereby dramatically increasing the efficiency of simultaneous two-photon excitation. For example, when using continuous wave excitation the efficiency of two-photon excitation for a particular molecular system may be $10^5$ smaller than that achieved with single-photon excitation. However, if the same average optical power is emitted in the form of a train of very short pulses, the shift in product of the peak and average powers can change this ratio such that it is close to unity.

Figure 2:
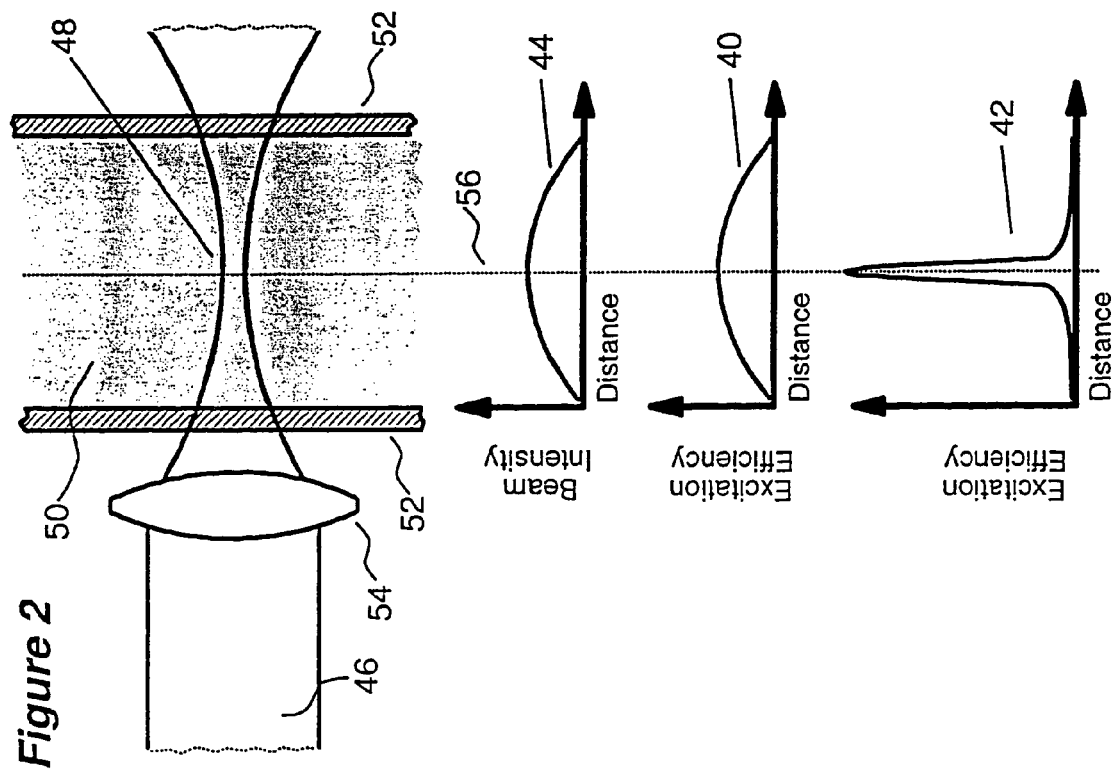
FIG. 2 shows the relationships between incident power distribution and excitation efficiency for single-photon and two-photon excitation.

The non-linear nature of simultaneous two-photon excitation can be exploited to achieve an important difference in the spatial excitation properties of simultaneous two-photon excitation compared to linear excitation. For example, FIG. 2 shows that the single-photon excitation efficiency profile 40 and the simultaneous two-photon excitation efficiency profile 42 differ dramatically as a function of the beam intensity profile 44 when a laser beam 46 is focused 48 into a material 50. This material 50 might be a laser dye solution held between the walls of a cuvette 52. Another example of this material 50 might be human tissue underneath skin. Focussing 48 of the laser beam 46 with a lens 54 produces a beam intensity profile 44 that varies as a function of distance through the sample 50, reaching a maximum level at the center of the focus 56 as predicted by classical Gaussian optical theory. For a single-photon process, the linear relationship between beam intensity (or incident power) and excitation efficiency results in a single-photon excitation efficiency profile 40 that linearly follows the beam intensity profile 44. In contrast, for the simultaneous two-photon process, the non-linear relationship between beam intensity (or incident power) and excitation efficiency results in a simultaneous two-photon excitation efficiency profile 42 that follows the square of the beam intensity profile 44. Hence, focussing 48 the laser beam 46 can be used to substantially limit the extent of excitation to a small focus zone, or confocal region, when simultaneous two-photon excitation is employed. In contrast, when linear excitation is employed, excitation occurs substantially along the entire optical path, making spatial localization of excitation considerably less defined.

Figure 3:
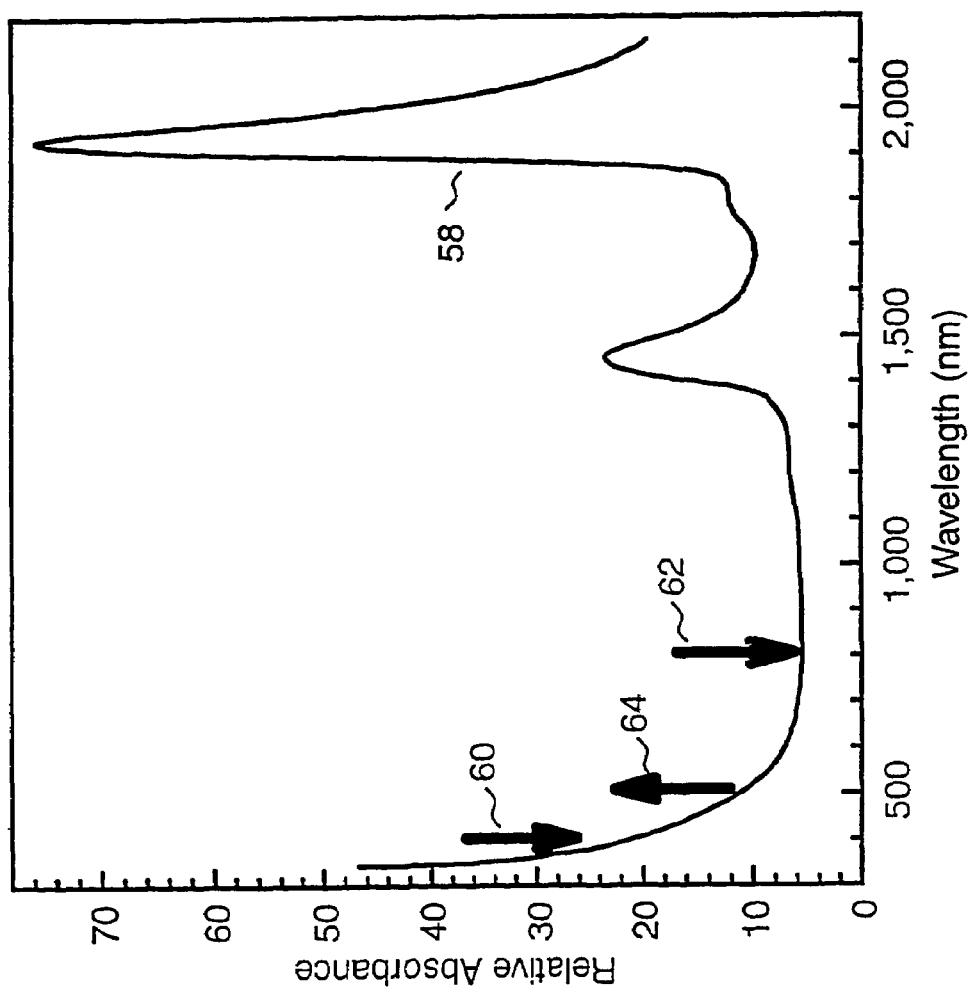
FIG. 3 shows an example absorption spectrum for animal tissue covering the ultraviolet to near infrared spectral region.
Figure 4:
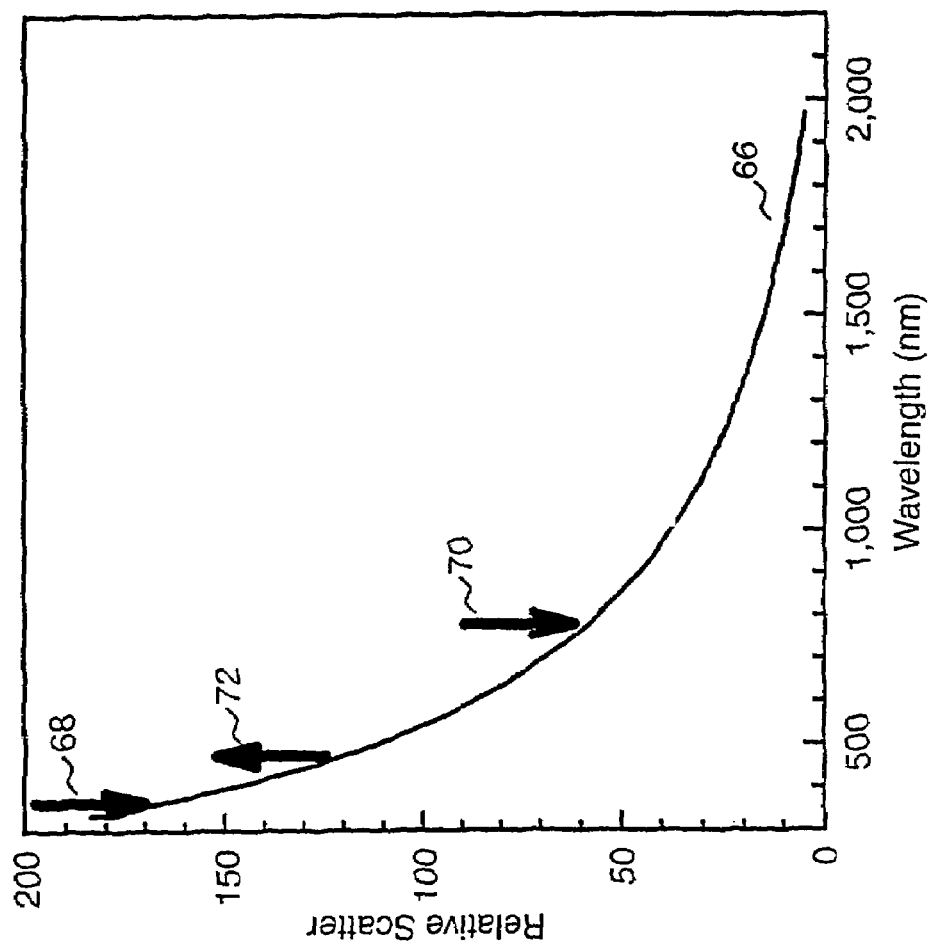
FIG. 4 shows a scattering spectrum for animal tissue covering the ultraviolet to near infrared spectral region.

Comparison of Linear and Non-Linear Excitation—Absorption and Scattering Effects:

While the cross-section for simultaneous two-photon excitation may be considerably lower than that observed with single-photon excitation, use of simultaneous two-photon excitation may be favorable to single-photon excitation under many conditions because of lower matrix absorption and optical scattering of longer wavelength optical radiation. For example, FIG. 3 shows an absorption spectrum 58 for animal tissue, such as human dermis or liver, covering the ultraviolet (UV) to near infrared (NIR) spectral region. FIG. 4 shows a scattering spectrum 66 for animal tissue, such as human dermis or liver, under similar conditions. Specifically, FIG. 3 demonstrates how higher-energy photons 60, such as those used for linear excitation of diagnostic agents, may experience considerably greater tissue absorption than lower-energy photons 62, such as those used for non-linear excitation of diagnostic agents. For instance, human skin strongly absorbs higher-energy photons 60 at 400 mm, but is relatively transparent to lower-energy photons 62 at 800 nm. This is a consequence of the relatively high natural absorbance of higher-energy photons 60, having ultraviolet or visible wavelengths, by pigments, proteins, and genetic materials, among other natural components, of skin. Note also the relationship between excitation energies and the emission wavelength 64 of the diagnostic agent. Regardless of whether higher-energy photons 60 or lower-energy photons 62 are used to excite the agent, the emission wavelength 64 will occur at an energy that is determined by the agent, not the excitation method applied to the agent. FIG. 4 further demonstrates how higher-energy photons 68 may experience considerably greater tissue scatter than lower-energy photons 70. Any optically dense medium, such as human skin, will strongly scatter higher-energy photons 68 at visible or ultraviolet wavelengths, for example at 400 nm, but will exhibit much lower scatter for lower-energy photons 70 at NIR or infrared (IR) wavelengths, for example at 800 nm. Note that as shown earlier in FIG. 3, FIG. 4 shows that the emission wavelength 72 of the diagnostic agent will typically fall between that of the higher-energy photons 60 and the lower-energy photons 62.

These differences in optical properties have several important consequences. First, absorption of short-wavelength, higher-energy photons 60 by tissue can result in undesirable tissue damage. In contrast, negligible effects may be experienced under irradiation with lower-energy photons 62, such as NIR light, even when the optical power of the NIR light is many-fold higher than that of the UV or visible radiation. Second, the inherently high absorption and scatter of higher-energy photons 68 by tissue can result in very shallow tissue penetration depths, while lower-energy photons 70 generally have much greater penetration depths. Since scattered higher-energy photons 60 will induce emission from diagnostic agents along their scatter path, higher-energy photons 60 that manage to penetrate tissue will tend to produce a diffuse emission zone that extends perpendicularly to the excitation path; but because of the quadratic dependence on two-photon excitation, irradiation with lower-energy photons 62 will produce a more sharply defined excitation pattern that is not significantly blurred by the presence of scattered lower-energy photons 62. Hence, illumination and subsequent detection of subsurface features is difficult or impossible when using higher-energy photons 68, such as those in the UV or visible spectral regions; in contrast, illumination and subsequent detection of subsurface features is much easier when using lower-energy photons 70, such as those in the NIR or IR spectral regions. Note also that the emitted light from the diagnostic agent may be highly absorbed and scattered by the tissue or other optically dense medium under examination. However, for satisfactory detection of the emitted light, it is only necessary that a small fraction of this light make its way to a detector. The large extent to which this emitted light may be scattered implies that sophisticated methods are needed to differentiate emitted light produced by an excited agent from scattered light and other optical or instrumental noise sources. This latter consideration is the topic of a subsequent section.

Figure 5:
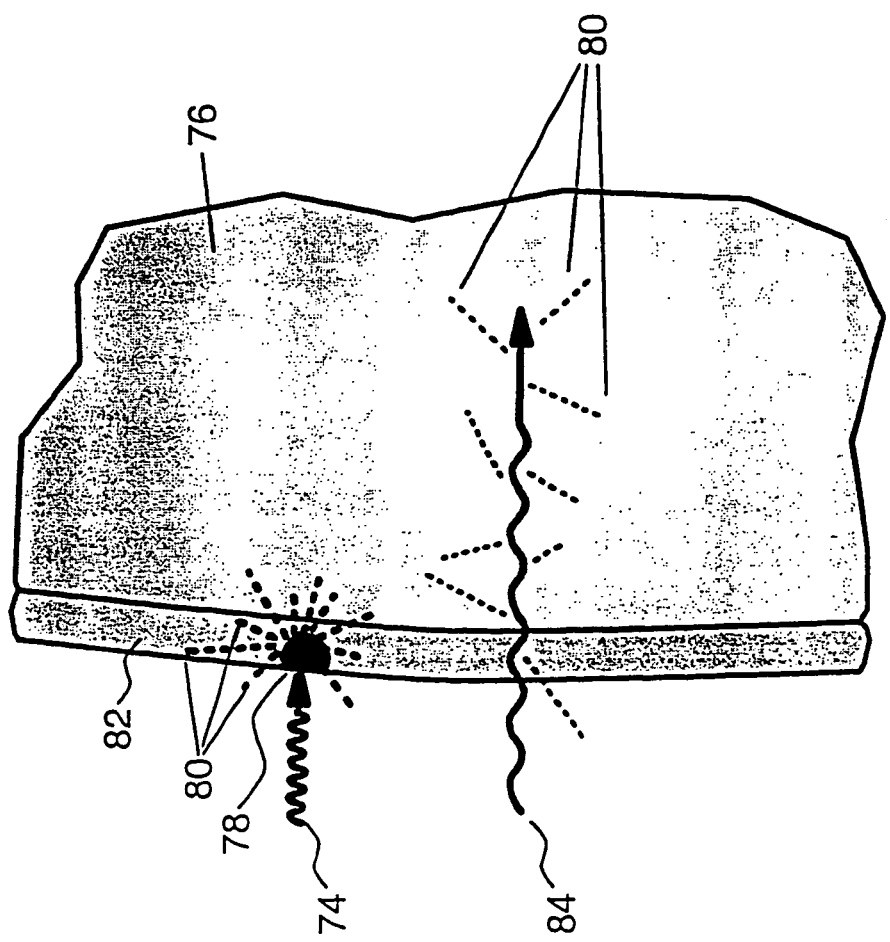
FIG. 5 shows the general trends in optical absorption and scattering properties of tissue for incident short wavelength and long wavelength light.

These important differences in absorption and penetration depth properties for higher-energy and lower-energy light are shown schematically in FIG. 5. When UV or visible light 74, for example light at 400 nm, impinges on human tissue 76, the majority of the optical energy is immediately absorbed 78 and scattered 80 in the outermost layers 82, such as the epidermis and dermis. Absorption 78 may occur due to excitation of certain molecules in the cells of this tissue 76, such as those composing the genetic material in the cellular nucleus, and can initiate a variety of collateral photochemical changes in these cells at the site of this absorption 78. These collateral photochemical changes can include irreversible genetic damage and induction of cancer. Hence, optical penetration depth is low and potential for induction of collateral damage is high for excitation with UV or visible light 74, such as that conventionally used for linear excitation of diagnostic agents. In contrast, NIR or IR light 84, for example at 800 nm, will experience much lower absorption and scatter 80 by tissue 76. The overall depth of penetration will be much greater and the extent of collateral damage to cells will be substantially lower. Hence, if long-wavelength excitation light is used in a two-photon excitation process to replace higher-energy, single-photon excitation, it becomes possible to photo-activate specific diagnostic agents present in deep tissues using relatively non-damaging wavelengths that have high penetration depths.

Figure 6:
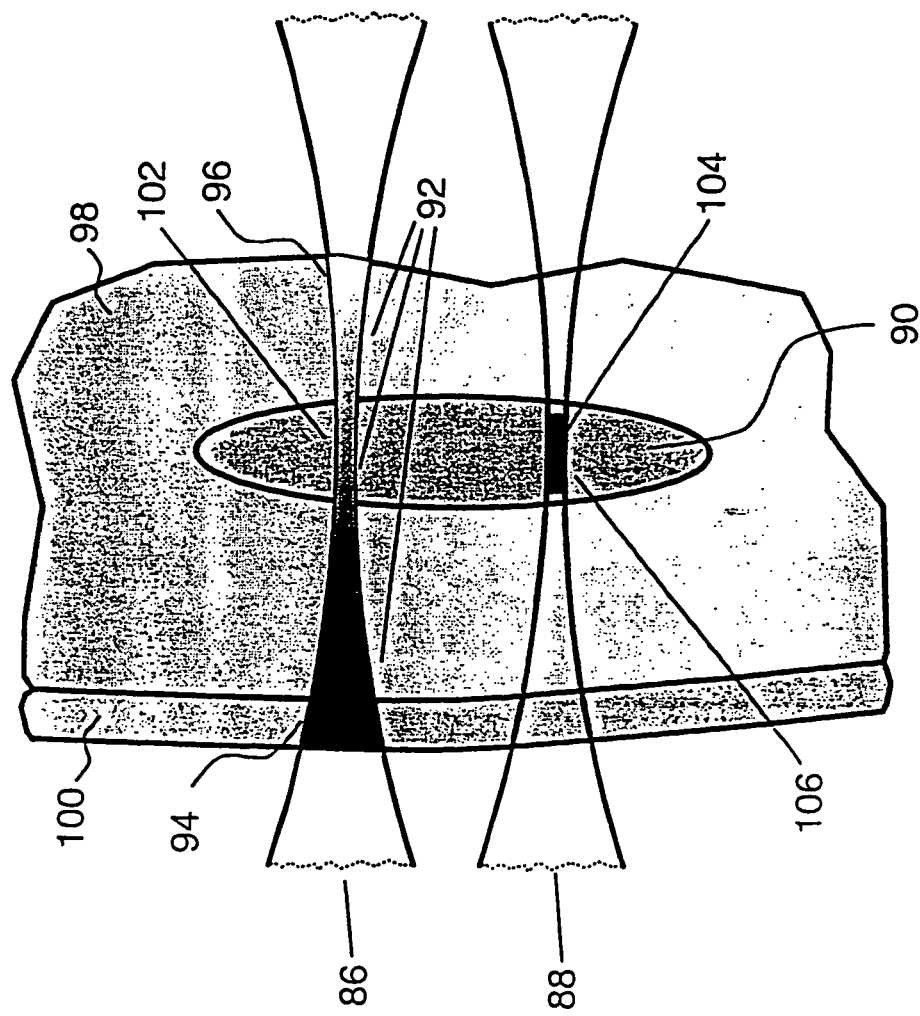
FIG. 6 compares optically-induced excitation regions in tissue when single-photon and two-photon excitation methods are used.

Furthermore, the salient properties of non-linear excitation shown in FIG. 2 have additional implications when coupled with the inherent non-damaging nature and high penetration depths possible with the use of NIR light. For example, FIG. 6 compares the penetration depth and spatial localization characteristics expected for single-photon excitation 86 and simultaneous two-photon NIR excitation 88 of imaging agents present in a subcutaneous tumor 90. Single-photon excitation 86 produces an excitation zone 92 that extends substantially along the entire optical path and has no significant specificity. Note that the efficiency of single-photon excitation 86 will vary alone the optical path due to absorption and scatter, being highest 94 near the point of introduction of optical radiation and dropping off rapidly 96 along the optical path. Note also that the potential for induction of collateral photo-damage will follow this same trend. Hence, single-photon excitation produces an extended excitation zone 92 that cannot be effectively limited to a finite volume, especially in deep tissues. Also, significant collateral damage can occur throughout surrounding tissues 98, and especially in surface tissues 100. If the single-photon excitation 86 is focussed, the excitation zone 92 will be slightly enhanced at the focus 102. Note, however, that this excitation zone 92 might not even extend all the way into the tumor 90 if the UV or visible light used for single-photon excitation 86 is significantly absorbed or scattered prior to reaching the tumor 90. In contrast, use of NIR simultaneous two-photon excitation 88 produces a sharply defined remote excitation zone 104 that is substantially localized to the focus 106 as a consequence of the intrinsic non-linear properties of this excitation method. Furthermore, because of the reduced absorption of NIR light, collateral damage to the surrounding tissues 98 and especially to surface tissues 100 is minimized. And as a consequence of the combined low absorption and scatter of NIR light, it is possible to effectively probe far deeper locations than those feasible using UV or visible wavelengths.

Figure 7:
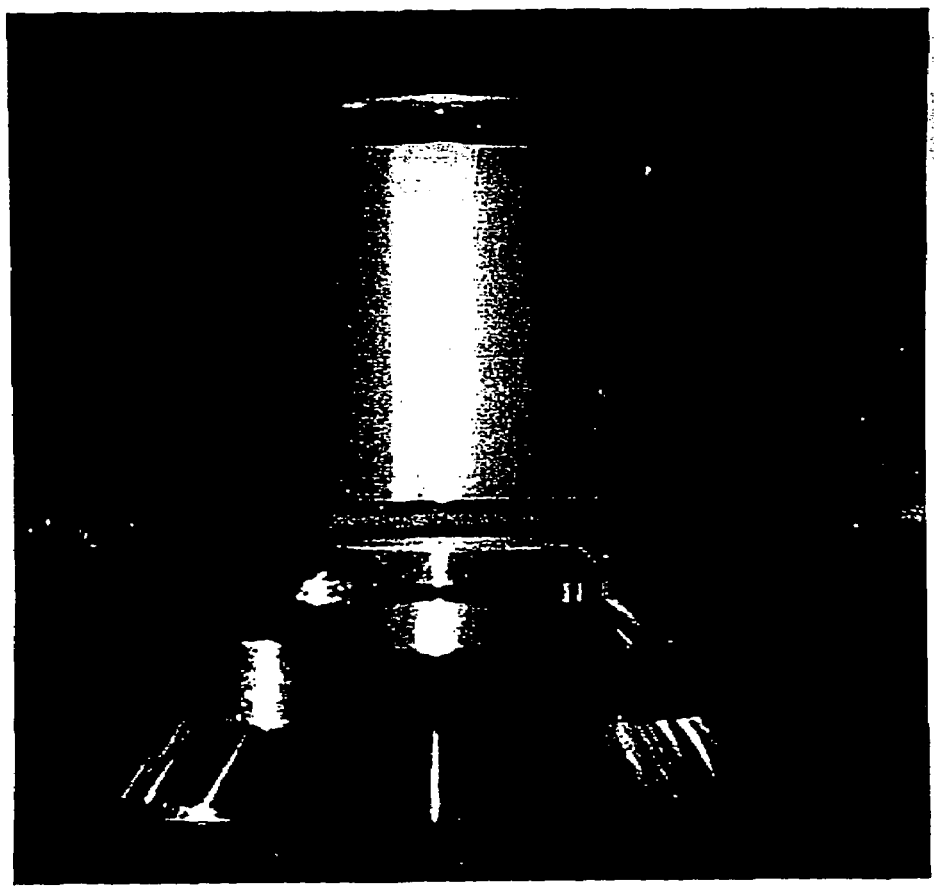
FIG. 7 shows typical properties of linear excitation of a diagnostic agent in solution.
Figure 8:
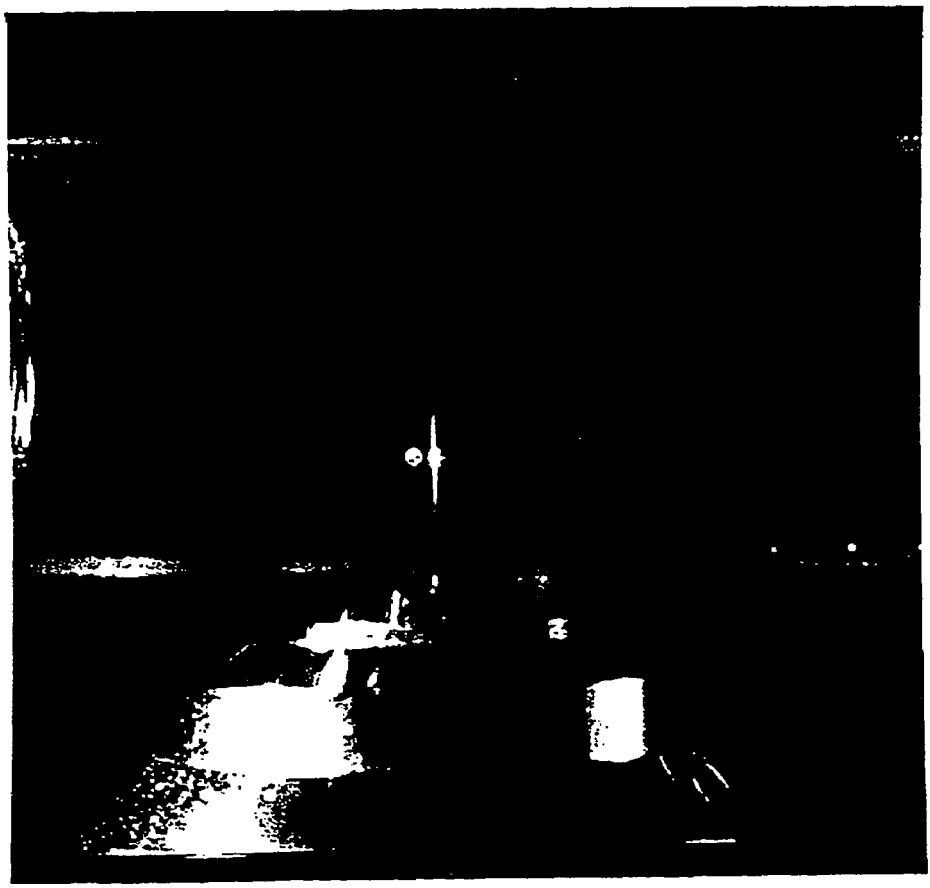
FIG. 8 shows typical properties of non-linear excitation of a diagnostic agent in solution.

Examples of Linear and Non-Linear Excitation of Typical Diagnostic Imaging Agents:

Linear excitation of a diagnostic a gent in solution is shown in FIG. 7. In this example, laser radiation at 442 nm was used to excite a dilute solution of the dye molecule FITC in methanol. The laser beam emitted from a continuous wave helium-cadmium laser was focused through a 20× microscope objective into a cuvette containing the dye solution, and stimulates a diffuse, elongated emission pattern in the dye. This example clearly shows that emission occurs along the entire optical path, and that a diffuse halo attributable to stimulation of the dye by scattered laser light surrounds the primary excitation path. In contrast. FIG. 8 demonstrates highly localized, remote photo-activation of a diagnostic agent using simultaneous two-photon excitation. In this example, laser radiation at 730 nm was used to excite a dilute solution of the dye molecule coumarin 480 in methanol. Specifically, the NIR output of a mode-locked titanium:sapphire laser, which emitted a continuous train of 730 nm wavelength, <200 fs pulses of light at a 78 MHz pulse repetition frequency in a beam approximately 1 mm in diameter, was focused through the same 20× microscope objective into a cuvette containing the dye solution. FIG. 8 clearly shows that fluorescence response from the dye molecule is limited to the focus of the NIR beam. Because of the quadratic relationship between two-photon excitation and instantaneous laser power, stimulation at positions along the excitation path prior to and following the focus is negligible. Also, no halo is observed, although a minor artifact attributable to overexposure of the photographic film is seen in this photograph around the emission zone.

Figure 9:
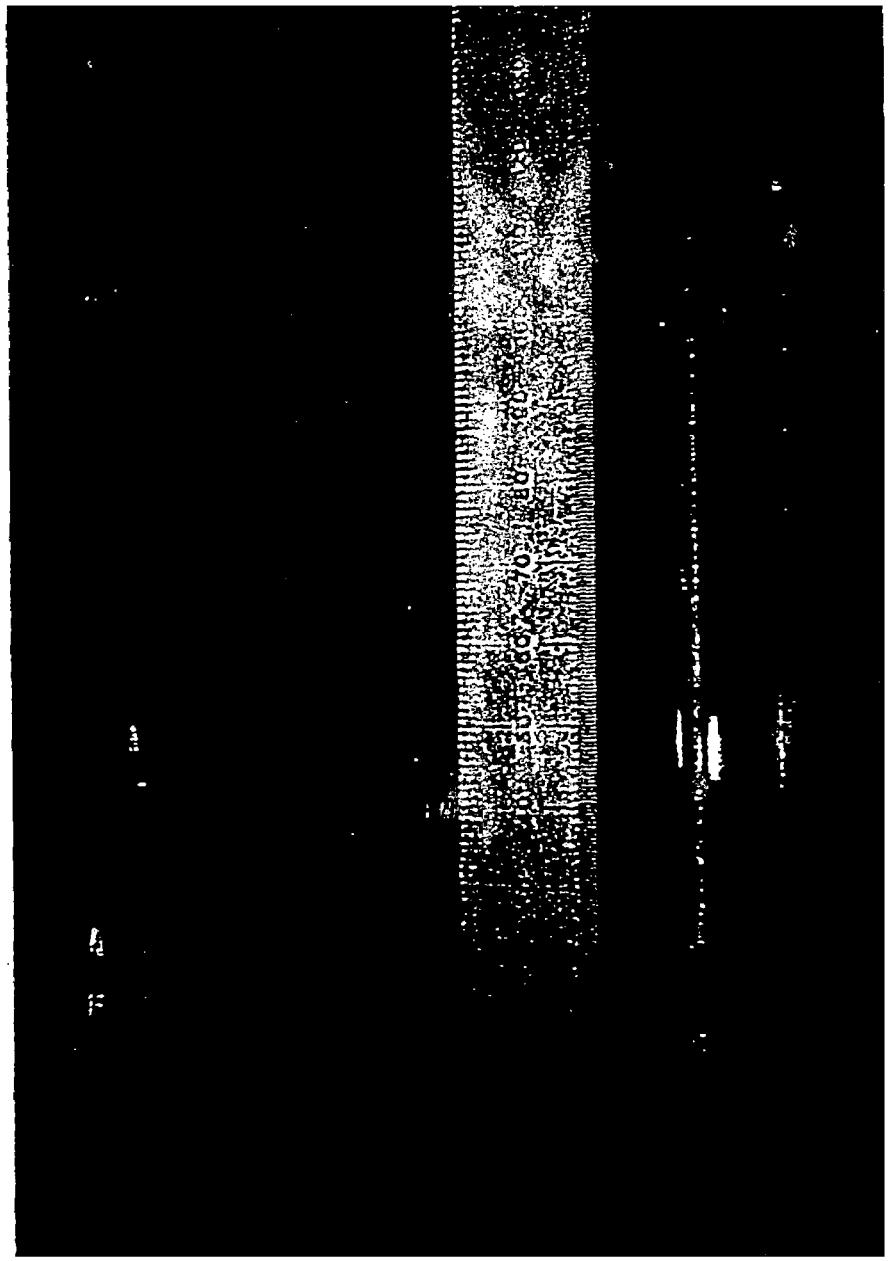
FIG. 9 shows a photograph of two-photon excited fluorescence of the dye molecule coumarin 480 distributed evenly throughout a tissue phantom.

Highly localized remote photo-activation of a diagnostic agent present throughout an optically dense medium is demonstrated in FIG. 9. This shows a photograph of two-photon excited fluorescence of the dye molecule coumarin 480 distributed evenly throughout a tissue phantom consisting of a block of agarose gelatin. NIR output of the mode-locked titanium:sapphire laser, which emitted a continuous train of 730 nm wavelength, 200 fs pulses of light at a 78 MHz pulse repetition frequency in a beam approximately 1 mm in diameter, was expanded to produce a collimated beam approximately 50 mm in diameter using a beam expanding telescope. This expanded beam was then focused into the gelatin block using a 100 mm focal length, 50 mm diameter biconvex singlet glass lens. The gelatin block was then positioned such that the focus of this 100-nm f.l. lens fell at a position 40 mm into the block. FIG. 9 clearly shows that fluorescence response from the coumarin 480 is only stimulated at the focus of the NIR beam. Because of the quadratic relationship between two-photon excitation and instantaneous laser power, stimulation at positions along the excitation path prior to and following the focus is negligible. Hence, little or no excitation or collateral photo-activation of damage can occur outside the focus region. Also, because the NIR excitation light is only weakly scattered by the gelatin, sharp focus is maintained at deep penetration depths into the block. Note that the sharpness of the focus is determined by Gaussian optical properties; hence, the length of the confocal region is easily adjusted by changing the optical parameters used for beam expansion and subsequent re-focusing.

Figure 10:
FIG. 10 shows a photograph of two-photon excited fluorescence of the dye molecule coumarin 480 distributed evenly throughout a tumor specimen.

Similar results are obtained if an equivalent excitation process is applied to a labeled tumor specimen, as shown in FIG. 10. This shows a photograph of two-photon excited fluorescence of the dye molecule coumarin 480 distributed evenly throughout a block of mouse carcinoma tissue. As in FIG. 9, a tightly localized site of activation is demonstrated, even for this sample having an extremely high optical density.

Excitation Sources for Two-Photon Excitation of Diagnostic Imaging Agents:

The relatively low cross-section for simultaneous two-photon excitation, which is typically about one hundred thousand-fold smaller than that for an equivalent single-photon excitation process, means that special optical excitation sources must typically be used to efficiently excite diagnostic agents. Optical sources that provide high peak powers can be used to substantially ameliorate the impact of this low efficiency by increasing instantaneous incident powers while maintaining modest average power levels. In fact, quasi-continuous wave mode-locked lasers, such as the mode-locked titanium:sapphire laser, are ideal for exciting molecular diagnostic agents in optically dense specimens, such as biological tissues. Specifically, such lasers are capable of delivering NIR peak powers in excess of 10 kW, but in the form of very high repetition rate (>25 MHz pulse repetition rate), ultra-short (~200 fs pulse duration), low energy (~1 nJ per pulse) pulses; partitioning of average laser power (on the order of 10 mW to 2 W) into a high frequency train of ultra-short pulses yields an excitation beam that is extremely efficient for stimulating two-photon excited fluorescence but is essentially harmless to biological materials. The quasi-continuous output of mode-locked or other high-repetition rate lasers is also highly compatible with various modulation methods, especially when the modulation is performed at frequencies considerably below the pulse repetition frequency of the laser, since the pulsed nature of the source can be ignored in the subsequent demodulation process.

The specific example of the mode-locked titanium:sapphire laser is continuously tunable over a wavelength band extending from approximately 690 nm to 1080 nm, which corresponds well to a region of minimal scatter and absorption for biological specimens. Two-photon absorption in this band also corresponds to an important single-photon absorption region, from 345 nm to 540 nm, for many possible diagnostic imaging agents; while two-photon selection rules are sometimes quite different from corresponding single-photon selection rules, strong absorption for the single-photon process can be indicative of significant two-photon absorption at wavelengths approximately twice that of the single-photon wavelength.

It will be clear that, in addition to the mode-locked titanium:sapphire laser, various other optical sources are applicable for excitation of diagnostic imaging agents. Especially important are diode lasers, Nd:YAG and Nd:YLF lasers, and optical parametric oscillators, amplifiers and generators. Pulsed diode lasers offer attractive performance as a result of their extremely high operational efficiencies, and are available at a variety of wavelengths in the NIR. Mode-locked Nd:YAG and Nd:YLF lasers provide an efficient, reliable means for generating NIR excitation light at 1064 nm and at 1047 or 1053 nm, respectively. Mode-locked optical parametric oscillators, amplifiers and generators are capable of producing optical radiation covering a band from approximately 500 nm to greater than 3000 nm; availability of wavelengths from 1000 nm to 1800 nm affords a practical means for exciting diagnostic agents using light in a band of exceptionally low tissue scatter and absorption, and may be especially useful for activation of NIR diagnostic agents (ie, those that have single-photon absorption bands at wavelengths in excess of 500 nm). Also, various other pulsed or mode-locked lasers have applicability, including: argon ion lasers; krypton ion lasers; helium-neon lasers; helium-cadmium lasers; ruby lasers; Nd:YAP, Nd:YVO4, Nd:Glass, and Nd:CrGsGG lasers; regeneratively amplified lasers; Cr:LiSF lasers; Er:YAG lasers; F-center lasers; Ho:YAF and Ho:YLF lasers; and copper vapor lasers. Various continuous wave lasers may also be used, but with considerably lower efficiency than that achieved using pulsed lasers.

Detection of Two-Photon Excited Emission from Diagnostic Imaging Agents:

Spatial information concerning the origin of the emitted light from a two-photon excited diagnostic imaging agent is encoded by and may be correlated to the excitation focus. This is in stark contrast with single-photon excited imaging methods, including those based on photon migration, where the diagnostic imaging signal must be carefully deconvolved from emission light generated along the entire excitation path and from emission produced by scattered excitation light. Hence, it is not necessary for the light emitted from the two-photon excited diagnostic agent to be detected or imaged directly without scatter. In fact, it is only necessary that a fraction of this emitted light be collected and detected in such a way that the collection and detection process does not distort the correlation between detected signal and emission point of origin.

To understand the significance of the relationship between signal detection and two-photon excited emission point of origin, it is useful to consider what happens to the emitted light immediately following the instant of emission. When imaging in an optically dense specimen, such as biological tissue, light from the two-photon excited diagnostic imaging agent will be emitted in an essentially isotropic manner. Some fraction of this emitted light will travel directly to a detector apparatus mounted remotely from the point of emission, while some other fraction will travel a circuitous route to the detector apparatus as a consequence of one or more scattering events occurring between emission and detection. If an attempt is made to image at a depth of 10 cm in a biological specimen, the transit time for an unscattered, or ballistic, emitted photon (that is, the total transit time from instant of emission to exit from a surface of the specimen) will be approximately 0.3 ns: for a highly scattered emitted photon, this transit time could be as high as 3-10 ns. Thus, for maximum efficiency in this example, it would be desirable to integrate all of the emitted light for a period of time sufficient to capture most or all of the ballistic and highly scattered photons. This implies that for imaging at depths of 10 cm or less, an integration period of approximately 10 ns would be appropriate.

If an image is to be generated by moving or scanning the location of the excitation focus relative to the specimen, the foregoing analysis implies that the excitation point should not be moved more frequently than once every 10 ns. In fact, practical limitations on scanning processes and mechanisms, combined with signal-to-noise arguments concerning minimum dwell times and the additional possible use of modulation methods, mandate that scanning be performed using dwell times in excess of 1 µs. Thus, for intensity based imaging with dwell times in excess of 1 µs and possible modulation frequencies of 1 MHz or less, it makes little difference where the detector is located as long as it is situated such that it can collect a significant portion of the ballistic and scattered emitted light (the choice of location of detector relative to the emission point of origin, and hence the length of time introduced due to optical delay, has little or no effect on the ability to correlate the detected signal with its origin because of the short transit time relative to other measurement parameters). Accordingly, it will be clear that the detector may be located in such a way that it comprises an epi-illumination configuration with the excitation beam, or that it may be located externally to the excitation beam. It is notable that the epi-illumination configuration (or other possible co-linear excitation and detection configurations) minimizes potential parallax losses for detection of surface or near surface objects, but that such configurations are more susceptible to interference from elastically scattered or reflected excitation light. Parallax losses may be minimized for external detection configurations by actively orienting the detection system such that it maintains consistent registry with the point of excitation, by using multiple detection assemblies that are individually optimized for collection of emitted light from different zones within the specimen, or by locating the detection system sufficiently far from the specimen such that parallax losses are minimal.

The discussion on detection of emitted light from two-photon excited diagnostic imaging agents has focused to this point on intensity based methods, wherein an image may be constructed by correlating detected intensity of emission with location of excitation for multiple excitation points throughout a specimen. However, intensity based methods are not always optimal, since they are susceptible to a number of complicating factors, including:

Variations in scatter and absorption of excitation light due to heterogeneities in the specimen—heterogeneities, such as areas of abnormal optical density, that are located between the excitation source and the intended point of excitation can translate into unanticipated differences in effective excitation level at the intended point of excitation. Artifacts caused by this phenomenon can be ameliorated by acquiring data along several excitation paths that are affected to different extents by this heterogeneity, followed by subsequent deconvolution of the resultant multiple data sets, but this may be difficult or impossible for some specimens.

Variations in scatter and absorption of emitted light due to heterogeneities in the specimen—heterogeneities, such as areas of abnormal optical density, that are located between the point of emission and the detection system can translate into unanticipated differences in collection efficiency for light emitted from the point of excitation. Artifacts caused by this phenomenon can be ameliorated by acquiring data along several collection paths that are affected to different extents by this heterogeneity, followed by subsequent deconvolution of the resultant multiple data sets, but this may be difficult or impossible for some specimens.

Variations in concentration or local environment of diagnostic imaging agents that are not directly correlated with form or function—it is assumed in intensity based imaging that changes in emission level throughout a specimen can be correlated with structural or physiological organization of the specimen. However, if the imaging agent is not appropriately distributed throughout the specimen, or if other factors, such as heterogeneity in the local environment within the specimen, affect the emission of the imaging agent in ways that cannot be correlated with form or function, then it becomes harder to obtain meaningful data from the specimen. Artifacts caused by this phenomenon can be ameliorated by using or by designing imaging agents that are not susceptible to such factors, but this may be difficult or impossible for some specimens.

A detection approach that is less susceptible to optical heterogeneity of the specimen could be based on measurement of chance in excited state lifetime rather than on intensity of emission. Excited state lifetimes are an intrinsic property of the excited state of a molecular agent and its immediate environment, and fortuitously the accurate measurement of lifetimes are immune to all but the grossest variations in excitation level and collection efficiency. A convenient means for measuring excited state lifetimes uses phase photometric methods to correlate phase shift between a modulated excitation source and the resultant emission signal to lifetime. Specifically, the preceding discussion on photon transit times implies that phase photometric methods are applicable for imaging in optically dense media, especially for agents with lifetimes in excess of 1-10 ns. Hence, if diagnostic imaging agents are used that have emission lifetimes that correlate with form or function within the specimen, such as quenching of fluorescence of an imaging agent in the presence of oxygen or concentration of an imaging agent within a structure, then imaging based on change in lifetime rather than on emission intensity becomes practical. Such lifetime based methods would have equal applicability to laser scanning microscopy and to remote imaging of extended objects, such as a tumor in a human subject.

Appropriate collection devices for transduction of intensity or phase based emission data include, but are not limited to, photomultiplier tubes, microchannel plate devices, photodiodes, avalanche photodiodes, charge coupled devices and charge coupled device arrays, charge injection devices and charge injection device arrays, and photographic film.

Noise Reduction Methods for Recovery of Two-Photon Excited Emission from Diagnostic Imagine Agents—Modulation and Second Harmonic Detection:

The inherently low efficiency of the two-photon excitation process can translate into a very high ratio of scattered, unabsorbed excitation light to two-photon excited fluorescence emission. Furthermore, the importance of other possible linear interferences attributable to this very high excitation level, including single-photon excited fluorescence of the agent or other species present in the specimen under examination, Raman scatter, and other phenomena, along with the need to eliminate interferences from ambient light and other optical or electronic noise sources, all indicate that a modulated excitation method coupled with appropriate demodulation of the detector signal should provide optimal discrimination against interferences and enhanced recovery of the analytical signal. In fact, interferences from background reported by Denk et al. (U.S. Pat. No. 5,034,613) could be largely circumvented if suitable modulation and demodulation methods were used, including demodulation at the pulse repetition frequency of the laser; use of such methods would dramatically improve signal-to-noise (SNR) performance of their microscope. In general, modulation can improve detection performance for virtually any measurement in one or more ways:

(1) Rejection of continuous background or noise sources—in the example of Denk's two-photon laser scanning microscope, modulation of the excitation source with subsequent demodulation of the detector signal, using a device such as a lock-in amplifier (LIA) or a heterodyne demodulator, would limit detection system response to a band of frequencies closely related to the modulation frequency. By controlling the phase sensitivity of this demodulation, additional discrimination would be achieved against signals that are not linked to or closely matched with the modulation pattern. Hence, by suitable selection of modulation frequency and demodulation phase, interferences from noise sources such as room light or electronic noise at specific frequencies, for example from a nearby electric motor, can be strongly rejected. This approach is equally valid for remote imaging of extended objects, such as a tumor in a human subject.

(2) Rejection of broadband or "pink noise" sources—the measurement environment, along with the electronics and other devices used for any measurement, contribute broadband noise, sometimes called pink noise, into any measurement. The impact of this intrinsic noise can be greatly reduced through the use of bandwidth-limited detection methods. Specifically, for a given optical measurement, the observed signal voltage, $V_{SIGNAL}$, is related to a detector input current, $i_{INPUT}$, produced by photons interacting with a detector, multiplied by the input impedance, $Z_{INPUT}$, and the gain of the detection system, G, according to the following:

$$V_{SIGNAL} = i_{INPUT} \cdot Z_{INPUT} \cdot G, \quad (1)$$

while the observed noise voltage, $V_{NOISE}$, may be approximated by the product of the noise current, $i_{NOISE}$, the input impedance, the square root of the electronic or optical bandwidth, B, of the detection system, and the gain, according to following:

$$V_{NOISE} = i_{NOISE} \cdot Z_{INPUT} \cdot B^{1/2} \cdot G. \quad (2)$$

Hence SNR may be estimated from the ratio of these two voltages, ($V_{SIGNAL}/V_{NOISE}$). When a typical optical detector, such as a photomultiplier tube (PMT), is used to detect an unmodulated fluorescence signal, this detector will produce a certain signal level along with a noise current. For an example PMT, such as the Hamamatsu R928 (7.4×10$^5$ A/W radiant anode sensitivity), an optical input at a level of 10 pW produces 7.4 μA $i_{SIGNAL}$. If this signal current is converted to voltage in a low noise amplifier having a gain of 100, an input impedance of 50Ω, an input noise level of 5 nV/$\sqrt{Hz}$, and a bandwidth of 1 MHz, the following signals are produced:

$$V_{SIGNAL} = 7.4 \mu A \cdot 50 \, \Omega \cdot 100 = 37 \, mV;$$

$$V_{NOISE} = 5 \, nV/\sqrt{Hz} \cdot (10^7 \, Hz)^{1/2} \cdot 100 = 1.6 \, mV.$$

Note that Ohm's Law, or V=i·R, has been substituted for noise current and impedance shown in Eq. 2. Thus, for this broadband example, SNR=23. If this excitation energy is modulated, for example sinusoidally at 1 MHz with a 100% depth of modulation, the value of $V_{SIGNAL}$ will decrease to approximately 18.5 mV (assuming that this modulation is introduced by cyclic attenuation or other loss-based modulation method that results in an overall loss of 50% of average power without changing peak excitation power). But if the detection system uses bandwidth limited demodulation at 1 MHz having a bandwidth of 1 kHz, the pink noise decreases far faster than the signal:

$$V_{NOISE} = 5 \, nV/\sqrt{Hz} \cdot (10^3 \, Hz)^{1/2} \cdot 100 = 16 \, \mu V,$$

and the overall SNR increases to approximately 1200. Thus, although some signal strength is lost when using many forms of modulation, the overall increase in SNR more than compensates for this loss. Further, if there is any linear interference in the detector response, for example from ambient light leakage into the detector, the broadband detection scheme will detect this as an additional noise source, while the modulated, bandwidth limited scheme will reject this interference. Assume that ambient leakage produces a background signal of 1 μA on the PMT, which translates to 5 mV of background signal. For the unmodulated case, optical shot noise from this background, B, is equal to the square root of the total photons detected, and SNR≈S/(S+B)$^{1/2}$; this yields an estimated SNR of approximately 5.7. Notably, the SNR for the modulated case is essentially unchanged. This analysis is equally applicable to laser scanning microscopy and to remote imaging of extended objects, such as a tumor in a human subject.

(3) Rejection of linear interferences at the modulation frequency—as a consequence of the inherently low efficiency of the two-photon excitation, the ratio of scattered, unabsorbed excitation light to two-photon excited fluorescence emission is generally quite high. This includes linear interferences at the modulation frequency that arise from elastic and inelastic scatter as well as from single-photon excited fluorescence. Optical filtering is frequently used in an effort to spectrally distinguish two-photon emission from these optical background phenomena. Unfortunately, these interferences can be exceedingly difficult or impossible to eliminate using spectral means alone. As an alternative to ignoring these residual interference sources, one common approach for recovery of pure two-photon signal utilizes regression of the detected signal at several excitation power levels against excitation power level, so that the quadratic two-photon excited fluorescence component can be extracted mathematically from linear interferences; this makes use of a model of total fluorescence response, $I_f$, given by:

$$I_f = \alpha I_L + \beta I_L^2 \quad (3)$$

where $I_L$ is the instantaneous excitation intensity, α is a proportionality constant for various linear effects, and β is a proportionality constant for two-photon excited fluorescence. While this regression-based method is appropriate for laboratory use where the necessary number of measurements per unit of time is small, it is too time consuming, complicated, and impractical whenever total data acquisition time must be minimized, such as in the case of multiple point scanned optical imaging. Far faster results can be obtained through the use of temporal rejection methods, such as second harmonic detection, which eliminates the need for performing multiple measurements at several power levels. Freeman et al. (R. G. Freeman, D. L. Gilliland and F. E. Lytle, "Second Harmonic Detection of Sinusoidally Modulated Two-Photon Excited Fluorescence," Analytical Chemistry, 62 (1990) 2216-2219) teach of second harmonic detection methods useful for the analysis of chemical samples, wherein sinusoidal modulation of the excitation source is used to generate a signal at twice the modulation frequency that is related only to two-photon excited fluorescence. A lock-in amplifier referenced to the modulation frequency is used to recover the pure two-photon signal at the second harmonic of the modulation frequency. While the second harmonic fluorescence signal is only approximately 12% of the total two-photon fluorescence produced, the improved rejection of linear interferences more than compensates for the loss in absolute signal level, resulting in an increase in the overall SNR. Hence, the second harmonic detection method is ideally applicable to laser scanning microscopy and to remote imaging of extended objects, such as a tumor in a human subject, as a consequence of its intrinsic efficiency in rejection of scatter and its high data bandwidth potential. These advantages mean that an imaging system using second harmonic detection can reliably obtain pure two-photon excited emission signals with minimal dwell times at each point, and with use of maximum excitation power for each measurement at each point.

The preceding enumerated advantages for the use of modulation methods in two-photon excited diagnostic imaging apply equally well whether data is acquired based on measurement of emission intensity or excited state lifetime. In fact, lifetime measurements are most readily and sensitively measured using phase photometric methods that are based on determination of phase shifts between a modulation waveform and the detected signal. Hence, it is clear that modulation methods, including those based on second-harmonic detection, have important utility in the efficient detection of two-photon excited fluorescence, where they serve to eliminate interferences from ambient and instrumental noise sources as well as from scattering and other phenomena occurring within the specimen undergoing examination. For optically dense media, such as human tissue, the extremely high ratio of scattered, unabsorbed excitation light to two-photon excited fluorescence emission makes use of such methods vital. Hence, for clinical imaging applications or for two-photon laser scanning microscopy, employment of modulation methods as described here will always be advantageous.

Contrast Agents in Two-Photon Excited Imagine—Endogenous and Exogenous Agents:

The foregoing discussion has shown that non-linear two-photon excitation can be used to effect important improvements in the specificity and depth of penetration for optically excitable molecular agents present in optically dense media, and that detection performance can be improved by use of encoding and decoding methods on the respective excitation and detection processes. The exceptional spatial localization of excitation possible when using two-photon methods can be harnessed to significantly improve contrast in the point of excitation. Once this localized excitation is effected, the analytic light thereby emitted may be detected using a variety of detection means. If this excitation point is caused to move relative to the specimen under examination, for example by scanning the position of the focus relative to the specimen or by scanning the position of the specimen relative to the focus, then a two- or three-dimensional image of the specimen can be generated by making a correlation between the location of the excitation point and the emitted light thereby produced. Useful contrast in this image, however, also depends on the existence of differences in the concentration or local environment of the molecular agent or agents responsible for emission. These agents may be endogenous or exogenous to the specimen, and imaging is ultimately based on contrasts in their localized emission properties that can be correlated to heterogeneity in structure or function within the specimen. Hence, it is important to also carefully consider the role of these contrast agents in non-linear diagnostic imaging.

Various endogenous chromophoric agents may be useful for diagnostic imaging, particularly of diseased tissue. Because of structural or physiological differences between diseased and non-diseased tissues, between various internal substructures and organs in higher animals, or between different ranges of healthy or sub-healthy tissues, the concentration or local environment of natural chromophoric agents, such as aromatic amino acids, proteins, nucleic acids, cellular energy exchange stores (such as adenosine triphosphate), enzymes, hormones, or other agents, can vary in ways that are useful for probing structural or functional heterogeneity. Thus, these endogenous indicators of heterogeneity can be probed non-invasively using two-photon excitation.

Unfortunately, in many cases the specificity possible with such agents is inadequate to achieve meaningful diagnostic imaging, and so exogenous agents must be added to the specimen. Traditional exogenous agents semi-selectively partition into specific tissues, organs, or other structural units of a specimen following administration. The route for administration of these agents is typically topical application or via systemic administration. Under ideal conditions, these agents will partition into or otherwise become concentrated on or in the structures of interest, or may be excluded preferentially from these structures. This concentration may be a consequence of isolated topical application directly onto a superficial structure, or through intrinsic differences in the physical or chemical properties of the structure which lead to partitioning of the agent into the structure. Contrast between areas of high concentration and low concentration can thereby be used as a basis for probing structural or physiological heterogeneity. Alternatively, exogenous agents may permeate throughout a specimen; if their emission properties, such as chromatic shift, quenching, or lifetime, are sensitive to physiological heterogeneity, then these parameters of the contrast agent can be used as the basis for contrast in imaging.

Because the emission properties of a molecular agent are determined by the fundamental properties of the excited state and its environment, the mechanism responsible for promoting the agent to the excited state has no significant impact on the emission properties of the excited state. Hence, a molecular diagnostic or contrast agent that works well under single-photon excitation conditions may be expected to exhibit similar behavior under two-photon excitation conditions. In general, any contrast agent that is useful for single-photon excitation can be used with two-photon excitation, where the enhanced control over site of excitation will serve to improve resolution of the image. Appropriate contrast agents include many molecular agents used as biological dyes or stains, as well as those used for photodynamic therapy (PDT). Standard PDT agents have tissue specificities that in general are based on the combined chemical and physical properties of the agent and the tissue, such as a cancerous lesion. These agents are efficient absorbers of optical energy, and in many cases are luminescent. For example,

- psoralen and its derivatives (including 5-methoxypsoralen [or 5-MOP]; 8-methoxypsoralen [8-MOP]; 4,5',8-trimethylpsoralen [TMP]; 4'-aminomethyl-4,5',8-trimethylpsoralen [AMT]; 4'-hydroxymethyl-4,5',8-trimethylpsoralen [HMT]; 5-chloromethyl-8-methoxypsoralen, Angelicin [isopsoralen]; 5-methlyangelicin [5-MIP]; and 3-carbethoypsoralen);
- various porphyrin and hematoporphyrin derivatives (including haematoporphyrin derivative [HPD]; Photofrin II; benzoporphyrin derivative [BPD]; protoporphyrin IX [Pp IX]; dye hematoporphyrin ether [DHE]; polyhematoporphyrin esters [PHE]; 13,17-N,N,N-dimethylethylethanolamine ester of protoporphyrin [PH1008]; tetra(3-hydroxyphenyl)-porphyrin [3-THPP]; tetraphenylporphyrin monosulfonate [TPPS1]; tetraphenylporphyrin disulfonate [TPPS2a]; dihematoporphyrin ether, meso-tetraphenyl-porphyrin; and mesotetra(4N-methylpyridyl)porphyrin [T4MPyP]) along with various tetraazaporphyrins (including octa-(4-ten-butylphenyl)-tetrapyrazinoporphyrazine [OPTP]; tetra-(4-tert-butyl) phthalocyanine [$t_4$-PcH$_2$]; and tetra-(4-ten-butyl) phthalocyanato-magnesium [$t_4$-PcMg]);
- various phthalocyanine derivatives (including chloroaluminum-sulfonated phthalocyanine [CASPc]; chloroaluminum phthalocyanine tetrasulfate [AlPcTS]; mono-, di-, tri- and tetra-sulphonated aluminum phthalocyanines [including AlSPc, AlS2Pc, AlS3Pc and AlS4Pc]; silicon phthalocyanine [SiPc IV]; zinc(II) phthalocyanine [ZnPc]; bis(di-isobutyl octadecylsiloxy)silicon 2,3-naphthalocyanine [isoBOSINC]); and Ge(IV)-octabutoxy-phthalocyanine;
- various rhodamine derivatives (including rhodamine-101 [Rh-101]; rhodamine-110 [Rh-110]; rhodamine-123 [Rh-123]; rhodamine-19 [Rh-191; rhodamine-560 (Rh-560]; rhodamine-575 [Rh-575]; rhodamine-590 [Rh-590]; rhodamine-610 [Rh-610]; rhodamine-640 [Rh-640]; rhodamine-6G [Rh-6G]; rhodamine-700 [Rh-700]; rhodamine-800 [Rh-800]; rhodamine-B [Rh-B]; sulforhodamine 640 or 101; and sulforhodamine B);
- various coumarin derivatives (including coumarin 1, 2, 4, 6, 6H, 7, 30, 47, 102, 106, 120, 151, 152, 152A, 153, 311, 307, 314, 334, 337, 343, 440, 450, 456, 460, 461, 466, 478, 480, 481, 485, 490, 500, 503, 504, 510, 515, 519, 521, 522, 523, 535, 540, 540A, 548);
- various benzophenoxazine derivatives (including 5-ethylamino-9-diethylaminobenzo[a]-phenoxazinium [EtNBA]; 5-ethylamino-9-diethylaminobenzo[a]phenothiazinium [EtNBS]; and 5-ethylamino-9-diethylaminobenzo[a]phenoselenazinium [EtNBSe]);
- chlorpromazine and its derivatives;
- various chlorophyll and bacteriochlorophyll derivatives (including bacteriochlorin a [BCA]);
- various metal-ligand complexes, such as tris(2,2'-bipyridine)ruthenium (II) dichloride (RuBPY);
- pheophorbide a [Pheo a]; merocyanine 540 [MC 540]; Vitamin D; 5-amino-laevulinic acid [ALA]; photosan; chlorin e6, chlorin e6 ethylenediamide, and mono-L-aspartyl chlorin e6; pheophorbide-a [Ph-a]; phenoxazine Nile blue derivatives (including various phenoxazine dyes);
- various charge transfer and rediative transfer agents, such as stilbene, stilbene derivatives and 4-(N-(2-hydroxyethyl)-N-methyl)-aminophenyl)-4'-(6-hydroxyhexylsulfonyl)stilbene (APSS); and
- numerous other photo-active agents, will in general become accumulated either at or near a point of application or semi-selectively within a specific tissue due to differences in the physical or chemical properties of the tissue which lead to partitioning of the PDT agent into the tissue; once accumulated, such agents will be susceptible to two-photon excitation, and their luminescent or other emission properties can used for acquisition of imagery data. Other photoactive agents that absorb light and are capable of subsequent energy transfer to one or more other agents may also be used, either alone or in conjunction with one or more responsive agents that are capable of accepting this transferred energy and transforming it into a radiative emission.

Biogenic Contrast Agents in Two-Photon Excited Imaging:

Under ideal conditions, standard contrast agents derive target specificity based on chemical or physical affinity for specific tissues. In this way, contrast agents partition into or otherwise become concentrated on or in tissues of interest. Unfortunately, this target specificity is usually not perfect. In fact, it is desirable to have an improved method for increasing specificity in the targeting of agent destination. A means for achieving such improvement in specificity is based on utilization of specific biological signatures of structure, function, or disease. For example, by a coupling anti-sense oligonucleotide agents to one or more photo-active moieties, such as FITC, new biogenic contrast agents are created that are capable of selectively tagging only specific cells, such as cancerous cells, that contain complementary genetic encoding. Moreover, the basic approach is easily extended to numerous genetic-based diseases or other disorders by changing the oligomeric code used for the biogenic probe. Employment of two-photon activation enables this powerful approach to be applied using the combined bio-specificity of the biogenic probe and the high spatial localization inherent to the simultaneous two-photon photo-activation process. Thus, very high contrast, very high resolution imaging becomes possible at the genetic level using agents that are specifically targeted for a particular organ, tissue, or lesion.

An optimal design for biogenic probes utilizes one or more photo-active moieties that have emission properties that change upon complexation between the biogenic agent and the target site. Specifically, changes in emission wavelength or lifetime upon complexation can be used to increase sensitivity of the general method, since such changes will help to increase contrast between areas containing complexed agent and those containing uncomplexed agent. An example is a biogenic agent based on a photo-active moiety that is quenched until complexation occurs, upon which occurrence emission becomes unquenched. Another example is an agent based on an intercalating photo-active moiety, such as psoralen, that is tethered to an anti-sense genetic sequence; upon complexation between the anti-sense sequence and its target sequence, intercalation of the photo-active moiety is enabled that leads to a chromatic shift in emission properties of the photo-active moiety.

It will be clear from the foregoing discussion that targeting methods based on other bio-specific means, such as immunological means, rather than solely on genetic means, are also covered within the scope of the invention. Specifically, agent specificity based on antigen-antibody methods, where an antibody probe is coupled to a photoactive group, provides a powerful new means for diagnosis of disease and infection. Additional means for achieving biospecificity in agent targeting include, but are not limited to, use of ligands, haptens, carbohydrate, lipid, or protein receptors or complexing agents, chelators, and encapsulating vehicles, such as liposomes, fullerenes, crown ethers, and cyclodextrins.

FIRST EXEMPLARY EMBODIMENT OF THE INVENTION

Figure 11:
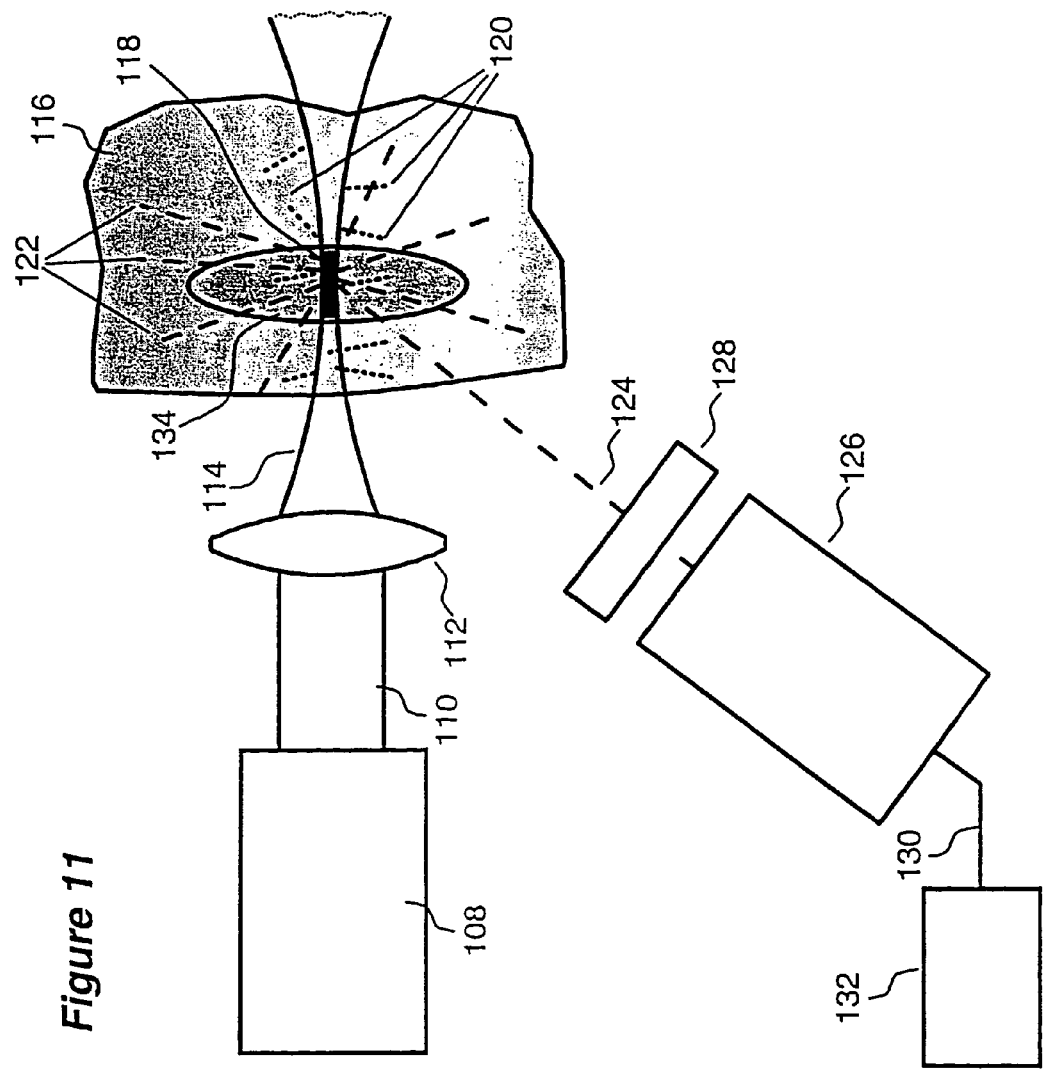
FIG. 11 shows a diagram of a specific preferred embodiment of the subject invention for imaging endogenous or exogenous diagnostic imaging agents.

Hence, it is a specific preferred embodiment of the subject invention to employ the output of a NIR source to induce simultaneous two-photon photo-activation of endogenous or exogenous diagnostic imaging agents present in a specimen using light at a wavelength approximately twice that necessary for conventional single-photon photo-activation. This preferred embodiment is shown in FIG. 11. The NIR Source 108 produces a beam of NIR radiation 110 consisting of a rapid series of high peak power pulses of NIR radiation. For example, standard commercially available mode-locked titanium:sapphire lasers are capable of outputting mode-locked pulses with durations <200 fs and pulse energies of about 20 nJ at pulse repetition frequencies in excess of 75 MHz; this source produces a quasi-continuous beam of light having a relatively low average power (up to several Watts) but high peak power (on the order of 100 kW) that is continuously tunable over a NIR wavelength band from approximately 690-1080 nm. The pulse train emitted by the NIR source 108 constitutes a beam of NIR radiation 110 that is easily focussed using standard optical means, such as reflective or refractive optics 112. The focused NIR beam 114 can then be directed onto a specimen 116 to be imaged. Simultaneous two-photon photo-activation of the diagnostic imaging agent will be substantially limited to the confocal region 118 of the focused beam 114 due to the high instantaneous irradiance level that is only present at the focus. Excitation light that is scattered 120 by the specimen 116 will not have a sufficient instantaneous irradiance level for significant excitation of any diagnostic imaging agent that may be present in areas outside of the confocal region 118. Light emitted 122 by diagnostic imaging agent molecules present in the confocal region 118 will exit the confocal region 118 in a substantially isotropic manner. A portion of the emitted light 124 is captured by a detection means 126, such as a photomultiplier tube, that is mounted at a position inside or outside of the specimen 116. This detection means 126 is fitted with a wavelength selection means 128, such as an optical bandpass filter, that serves to pre-process the captured portion of the emitted light 124 in such a way that the selection means 128 rejects a major fraction of the elastically scattered light while passing a major fraction of light at the wavelength or wavelengths corresponding to that which is principally characteristic of emission from the diagnostic agent. The signal thus issued 130 from the detection means 126 is captured by a processor means 132, the primary purpose of which is to record emission response from diagnostic imaging agent as a function of location of the confocal region 118. By causing the location of the confocal region 118 to be scanned throughout the volume of the specimen 116, a complete image of the specimen 116 may be obtained by examining the contents of the processor means 132 as a function of location of the confocal region 118. This image may be used to at identify zones of interest 134, such as subcutaneous tumors or other diseased areas.

SECOND EXEMPLARY EMBODIMENT OF THE INVENTION

Figure 12:
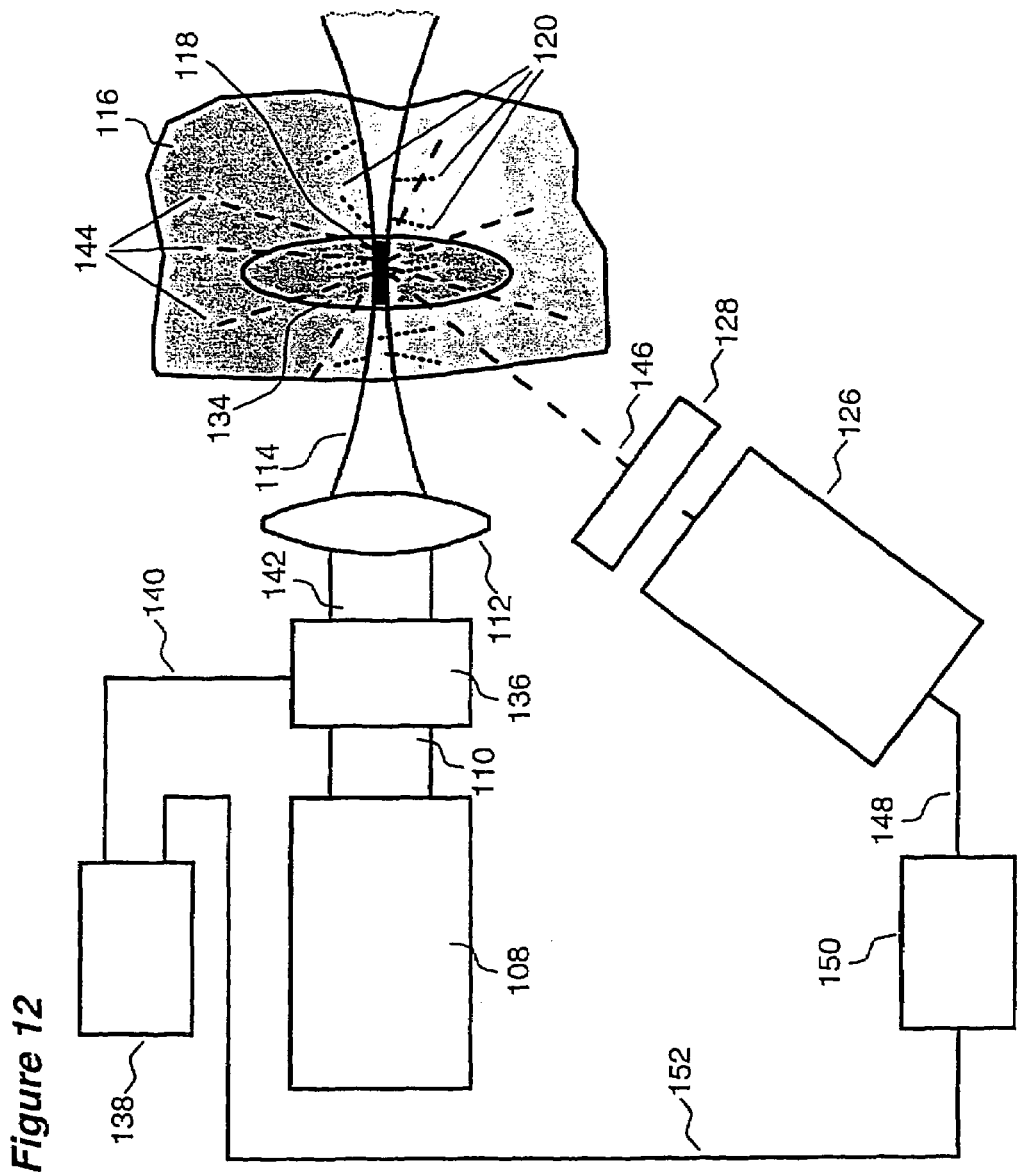
FIG. 12 shows a diagram of an alternate preferred embodiment of the subject invention for imaging endogenous or exogenous diagnostic imaging agents, wherein modulation is used to improve imaging performance.

As an alternate to this preferred embodiment, a modulation means may be incorporated into the general embodiment shown in FIG. 11; such modulation means may be used to improve overall performance of the imaging system, such as to improve rejection of environmental or instrumental noise sources, to enable recovery of pure two-photon excited emission at the second harmonic, or to facilitate detection of emitted light using phase photometric approaches. Specifically, FIG. 12 shows that a modulator means 136, such as an electro-optic or acousto-optic modulator, a chopper, or other means, located so as to interact with the beam of NIR radiation 110 emitted by the NIR source 108 can be used to encode the beam of NIR radiation 110 with a modulation pattern that is registered to the output of a modulator driver 138 that provides a drive signal 140 to the modulation means 136. The modulated beam of NIR radiation 142 thereby produced is then directed onto the specimen 116 as described previously for FIG. 11. The two-photon excited emitted light 144 thereby produced will exit the confocal region 118 in an essentially isotropic manner. However, in contrast to the similar emitted light 122 described previously for FIG. 11, this emitted light 144 will exhibit a modulation that is essentially synchronous with the modulation of the modulated beam of NIR radiation 142, which in turn is synchronous with the drive signal 140 issued by the modulator driver 138. A portion of the modulated emitted light 146 is captured by a detection means 126, such as a photomultiplier tube, that is mounted at a position inside or outside of the specimen 116. This detection means 126 is fitted with a wavelength selection means 128, such as an optical bandpass filter, that serves to process the captured portion of the modulated emitted light 146 in such a way that the selection means 128 rejects a major fraction of the elastically scattered light while passing a major fraction of light at the wavelength or wavelengths corresponding to that which is principally characteristic of emission from the diagnostic agent. The modulated signal thus issued 148 from the detection means 126 is captured by a processor means 150. The processor means 150 serves two primary purposes, firstly to demodulate the modulated signal thus issued 148 from the detection means 126 using a demodulation reference output 152 issued by the modulator driver 138, and secondly to record demodulated emission response from the diagnostic imaging agent as a function of location of the confocal region 118. Hence, by causing the location of the confocal region 118 to be scanned throughout the volume of the specimen 116, a complete image of the specimen 116 may be obtained by examining the contents of the processor means 150 as a function of location of the confocal region 118. This image may be used to identify zones of interest 134, such as subcutaneous tumors or other diseased areas.

THIRD EXEMPLARY EMBODIMENT OF THE INVENTION

Figure 13:
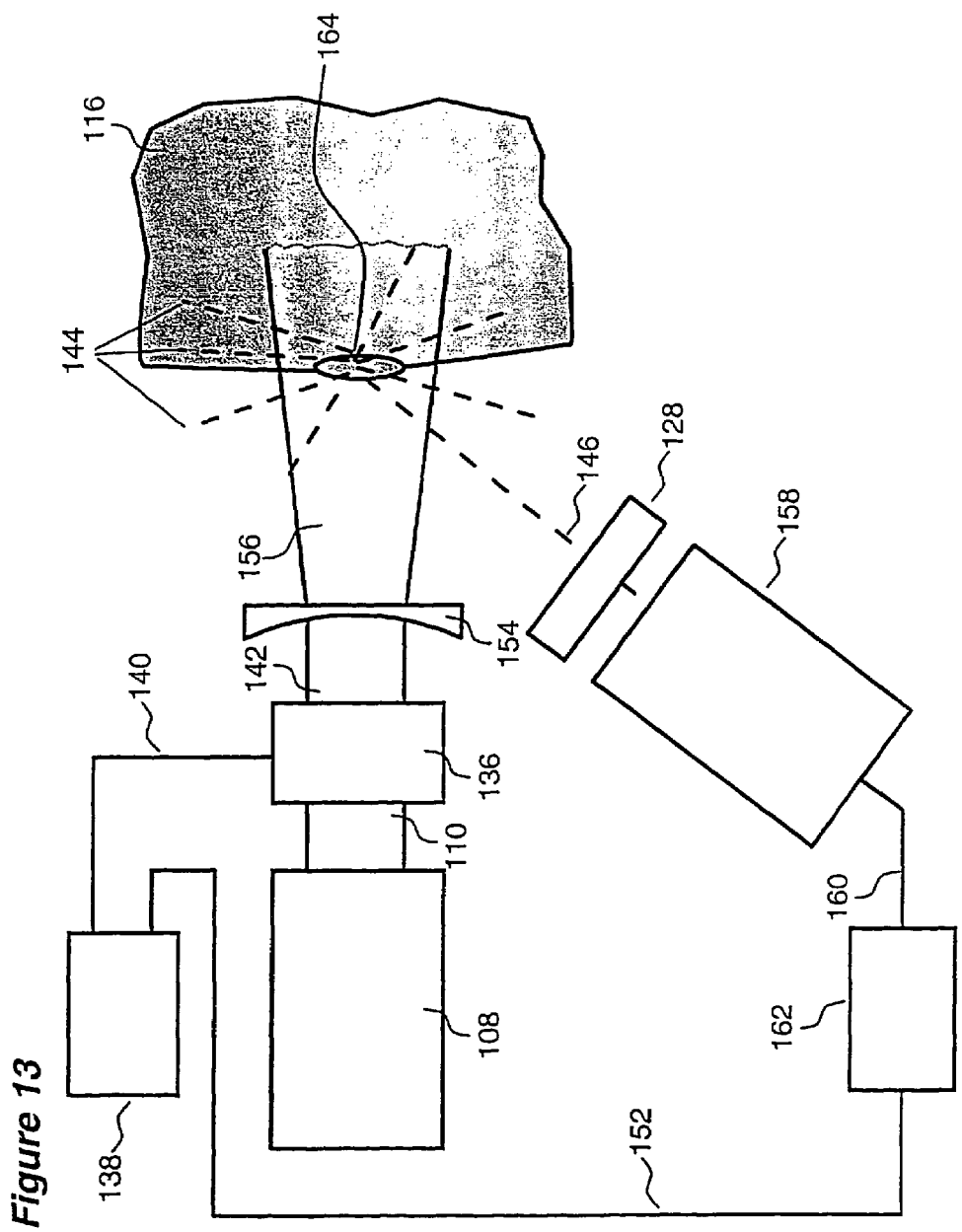
FIG. 13 shows a diagram of a second alternate preferred embodiment of the subject invention for videographic imaging of superficial features.

As a second alternate to this preferred embodiment, an unfocused beam of NIR radiation may be used to illuminate superficial features of a specimen to provide a direct imaging means of detection. This is shown in FIG. 13. Specifically, the output of a NIR source, such as the mode-locked titanium:sapphire laser, can be used to induce simultaneous two-photon photo-activation of endogenous or exogenous diagnostic imaging agents present on or near the surface of a specimen using light at a wavelength approximately twice that necessary for conventional single-photon photo-activation. The NIR Source 108 produces a beam of NIR radiation 110 consisting of a rapid series of high peak power pulses of NIR radiation. This beam is modulated using a modulation means 136 located so as to interact with the beam of NIR radiation 110 emitted by the NIR source 108. This modulator means 136 encodes the beam of NIR radiation 110 with a modulation pattern that is registered to the output of a modulator driver 138 that provides a drive signal 140 to the modulation means 136. The modulated beam of NIR radiation 142 thereby produced is then defocused using standard optical means, such as reflective or refractive optics 154, to produce a divergent excitation beam 156 that is directed onto a specimen 116 to be imaged. Simultaneous two-photon photo-activation of diagnostic imaging agent present on or near the surface of the specimen 116 produces modulated two-photon excited emitted light 144 having a modulation that is essentially synchronous with the modulation of the modulated beam of NIR radiation 142, which in turn is synchronous with the drive signal 140 issued by the modulator driver 138. A portion of the modulated emitted light 146 is captured by an imaging detection means 158, such as a charge coupled device array, that is mounted at a position outside of the specimen 116. This imaging detection means 158 is fitted with a wavelength selection means 128, such as an optical bandpass filter, that serves to process the captured portion of the modulated emitted light 146 in such a way that the selection means 128 rejects a major fraction of the elastically scattered light while passing a major fraction of light at the wavelength or wavelengths corresponding to that which is principally characteristic of emission from the diagnostic agent. The modulated signal thus issued 160 from the imaging detection means 158 is captured by a processor means 162. The processor means 162 serves two primary purposes, firstly to demodulate the modulated signal thus issued 160 from the imaging detection means 158 using a demodulation reference output 152 issued by the modulator driver 138, and secondly to record demodulated emission response from the diagnostic imaging agent as a function of location of emission. Hence, this alternate embodiment enables direct videographic imaging of surface features 164, such as skin cancer lesions, to be performed based on spatial differences in two-photon excited emission across the illuminated surface of the specimen 116.

It will be understood that each of the elements described above, or two or more together, may also find useful application in other types of constructions or applications differing from the types described above.

While the invention has been illustrated and described as embodied in a general method for improved selectivity in photo-activation of molecular diagnostic imaging agents, it is not intended to be limited to the details shown, since it will be understood that various omissions, modifications, substitutions and changes in the forms and details of the method illustrated and in its operation can be made by those skilled in the art without departing in any way from the spirit of the present invention. For example, in the third exemplary embodiment, the modulation and demodulation details may be omitted to produce a more simple imaging apparatus, although this example modification would yield an overall reduction in imaging performance.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. Imaging apparatus adapted for in vivo imaging a particular volume of plant or animal tissue containing at least one photo-active molecular agent, the apparatus comprising:

a source of collimated light, said light having a frequency effective to penetrate substantially into the tissue, said light being adapted to promote simultaneous two-photon excitation (TPE) of the molecular agent contained within the tissue;

beam expanding apparatus for expanding said collimated light into an expanded beam of collimated light;

focusing apparatus for focusing the expanded beam of collimated light throughout a range of focal lengths extending from a surface of said tissue to a depth substantially beyond said surface, said light source and focusing apparatus cooperating to promote TPE of the molecular agent, wherein a focal point or focal plane is adjustable over a distance of up to 100 mm with respect to said tissue;

a detector located proximate to the tissue and positioned to detect said light emitted by the molecular agent and which travels a path that does not retrace an optical path of the light incident on the tissue, said detector configured to produce a detected signal characteristic of the particular volume at which the light source has been focused;

a processor coupled to said detector; and a modulation system associated with said light source, said processor being coupled to said modulation system and adapted to produce a demodulated energy signal which is characteristic of the particular photo-activated molecular agent.

2. The apparatus of claim 1, wherein said light source produces a pulsed output having a pulse repetition frequency above about 75 megahertz and a sub-nanosecond pulse duration.

3. The apparatus of claim 2 wherein said light source produces near-infrared light.

4. The apparatus of claim 3 wherein said light source produces pulse energies of about 20 nanojoules.

5. The apparatus of claim 3 wherein said light source comprises a laser.

6. Apparatus adapted for in vivo medical diagnostic imaging comprising:

light source means for directing a confined light at and into tissue to be imaged, said light being selected in frequency and energy to penetrate below a tissue surface and to promote TPE substantially only at a confocal region at a distance of up to 100 mm below said tissue surface, said light source means including beam expanding means and focusing means cooperating together to shape said confocal region;

means for varying a position of a confocal region of the light within a range of depths in the tissue to be imaged;

detector means positioned to receive and detect isotropic radiation emitted by a photo-activated molecular agent within the tissue after said agent has been excited using two-photon excitation;

a modulator means for modulating said light with a type of modulation and producing a modulated light; and a processor coupled to said detector, said processor being coupled to said modulation system and adapted to produce a demodulated energy signal which is characteristic of said photo-activated molecular agent.

7. The apparatus of claim 6:
wherein the light source means includes means for producing a collimated light beam; and
wherein the light source means includes focusing means for focusing the collimated light beam to a confocal region located with tissue at a point below the tissue surface.

8. The apparatus of claim 7 wherein the means for producing a collimated light beam comprises a pulsed laser operating the near infra-red spectrum.

9. The apparatus of claim 6 wherein said imaging apparatus is a microscope.

10. An apparatus adapted for in vivo microscopic imaging to a distance of up to 100 mm within tissue comprising:
a light source, said light source producing a beam of light directed to or into a material to be imaged, wherein said light source includes beam expanding means and beam focusing means cooperating together to shape said beam of light into a confocal region, said light being selected in frequency and energy to penetrate into or below a surface of the material and to promote two-photon excitation substantially only in a confocal region to be imaged;
a modulator, said modulator cooperating with said light source to modulate said light with a type of modulation and produce a modulated light;
a detector positioned to receive and detect radiation emitted by a photo-activated molecular agent within the material after said agent has been excited using two-photon excitation; and
a demodulator, said demodulator coupled to said detector and producing a demodulated energy signal which is characteristic of the particular photo-activated molecular agent.

11. An apparatus according to claim 10 wherein said demodulator is a processor.

12. Apparatus adapted to in vivo medical diagnostic imaging comprising:
a light source, said light source producing light directed to or into deep tissue to be imaged, said light being selected in frequency and energy to penetrate into or below a surface of the tissue and to promote two-photon excitation substantially only in a region to be imaged;
a beam expanding apparatus adapted for expanding said light into an expanded beam of light;
a focusing apparatus adapted for focusing said expanded beam of light, said focusing apparatus being able to vary the position of the light within a range of depths in the region of tissue to be imaged, said range of depths extending up to 100 mm into said tissue to be imaged; and
a detector positioned to receive and detect radiation emitted by a photo-activated molecular agent within the material after said agent has been excited using two-photon excitation,
wherein said light source means includes means for producing a collimated light beam and focusing means for focusing the collimated light beam to a confocal region located with tissue at a point below the tissue surface.

13. An apparatus according to claim 12 wherein said light source produces near-infrared light.

14. An apparatus according to claim 13 wherein said light source is a laser.

15. An apparatus according to claim 12 further comprising a modulator, said modulator cooperating with said light to modulate said light with a type of modulation and produce a modulated light.

16. An apparatus according to claim 15 further comprising a demodulator, said demodulator coupled to said detector and producing a demodulated energy signal which is characteristic of the particular photo-activated molecular agent.

17. An apparatus according to claim 16, wherein said demodulator is a processor.

18. An apparatus according to claim 12 wherein said light source produces a pulsed output having a pulse repetition frequency above about 75 megahertz and a subnanosecond pulse duration.

19. An apparatus according to claim 12 wherein said light source produces pulse energies of about 20 nanojoules.

* * * * *